US011371034B2

(12) United States Patent
Hioki et al.

(10) Patent No.: US 11,371,034 B2
(45) Date of Patent: Jun. 28, 2022

(54) PRODUCTION METHOD FOR PROTEASE OF M23A SUBFAMILY

(71) Applicant: Kao Corporation, Tokyo (JP)

(72) Inventors: Takahiro Hioki, Wakayama (JP); Daichi Yamashita, Utsunomiya (JP); Masatoshi Tohata, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/961,459

(22) PCT Filed: Jan. 15, 2019

(86) PCT No.: PCT/JP2019/000894

§ 371 (c)(1),
(2) Date: Jul. 10, 2020

(87) PCT Pub. No.: WO2019/142773

PCT Pub. Date: Jul. 25, 2019

(65) Prior Publication Data

US 2021/0207116 A1 Jul. 8, 2021

(30) Foreign Application Priority Data

Jan. 16, 2018 (JP) ............................ JP2018-005193
Jan. 16, 2018 (JP) ............................ JP2018-005194
Nov. 22, 2018 (JP) ............................ JP2018-219142

(51) Int. Cl.
*C12N 9/50* (2006.01)
*C12N 1/20* (2006.01)
(Continued)

(52) U.S. Cl.
CPC ......... *C12N 9/6489* (2013.01); *C12N 15/625* (2013.01); *C12N 15/75* (2013.01)

(58) Field of Classification Search
CPC ......... C12N 9/52; C12N 15/75; C12N 15/625
See application file for complete search history.

(56) References Cited

U.S. PATENT DOCUMENTS

2006/0143738 A1* 6/2006 Lassen .................... C12N 9/52
800/288
2021/0071114 A1 3/2021 Yamashita et al.

FOREIGN PATENT DOCUMENTS

JP H04-108387 A 4/1992
JP 2003-116563 A 4/2003
(Continued)

OTHER PUBLICATIONS

Zhao. Elastolytic Mechanism of a Novel M23 Metalloprotease Pseudoalterin from Deep-sea *Pseudoalteromonas* sp. CF6-2: Cleaving Not Only Glycyl Bonds in the Hydrophobic Regions but Also Peptide Bonds in the Hydrophilic Regions Involved in Cross-Linking. JBC. vol. 287, No. 47, p. 39710-3970, Nov. 16, 2012.*
(Continued)

*Primary Examiner* — Yong D Pak
(74) *Attorney, Agent, or Firm* — Sterne, Kessler, Goldstein & Fox P.L.L.C.

(57) ABSTRACT

Provided is a method for efficiently producing an M23A family protease. The method for producing an M23A family protease includes culturing bacteria of the genus *Bacillus* having a polynucleotide encoding a proprotein of the M23A family protease introduced thereinto to produce a mature form of the M23A family protease extracellularly from the bacteria of the genus *Bacillus*.

8 Claims, 3 Drawing Sheets

Specification includes a Sequence Listing.

(51) Int. Cl.

| | |
|---|---|
| ***C12N 9/64*** | (2006.01) |
| ***C12N 15/62*** | (2006.01) |
| ***C12N 15/75*** | (2006.01) |

(56) References Cited

FOREIGN PATENT DOCUMENTS

| | | | |
|---|---|---|---|
| JP | 2019-122300 | A | 7/2019 |
| JP | 2019-122301 | A | 7/2019 |
| JP | 2019-123803 | A | 7/2019 |
| WO | WO 2015/158719 | A1 | 10/2015 |

OTHER PUBLICATIONS

Q8RQS6. UniProtKB/TrEMBL. Oct. 15, 2015.*
Kakeshita. Improvement of Heterologous Protein Secretion by Bacillus subtilis. Chapter 7. Advances in Applied Biotechnology. Jan. 20, 2012.*
International Search Report for PCT/JP2019/000894; I.A. fd Jan. 15, 2019, dated Mar. 19, 2019, from the Japan Patent Office, Tokyo, Japan.
International Preliminary Report on Patentability (IPRP), Chapter I of the Patent Cooperation Treaty, including the Written Opinion, for PCT/JP2019/000894; I.A. fd Jan. 15, 2019, dated Jul. 21, 2020, by the International Bureau of WIPO, Geneva, Switzerland.
Zhao, H-L et al., "Optimization of fermentation conditions for the production of the M23 protease Pseudoalterin by deep-sea *Pseudoalteromonas* sp. CF6-2 with artery powder as an inducer. Molecules." 2014;19(4):4779-4790. Published Apr. 16, 2014. doi: 10.3390/molecules19044779.
Gustin, JK et al., "A substitution at His-120 in the LasA protease of *Pseudomonas aeruginosa* blocks enzymatic activity without affecting propeptide processing or extracellular secretion." J Bacteriol. 1996;178(22):6608-6617. doi:10.1128/jb.178.22.6608-6617.1996.
Ahmed, K et al., "Purification, bacteriolytic activity, and specificity of β-lytic protease from *Lysobacter* sp. IB-9374." J Biosci Bioeng. 2003;95(I):27-34. doi:10.1016/S1389-1723(03)80144-5.
Hohmann, HP et al., "Host Organisms: *Bacillus subtilis*," in Industrial Biotechnology: Microorganisms, Wittman, C et al., eds., vol. 1, Chapter 7, pp. 221-297, ISBN 978-3-527-34179-5, Apr. 2017, Wiley.
Spencer, J et al., "Crystal structure of the LasA virulence factor from *Pseudomonas aeruginosa*: substrate specificity and mechanism of M23 metallopeptidases." J Mol Biol. 2010;396(4):908-923. doi:10.1016/j.jmb.2009.12.021.
Lowry, AG et al., "Purification and characterization of a novel zinc-proteinase from cultures of *Aeromonas hydrophila*." J Biol Chem. 1993;268(12):9071-9078.
Gökçen, A et al., "Biofilm-degrading enzymes from *Lysobacter gummosus*" Virulence. 2014;5(3):378-387. doi:10.4161/viru.27919 including the Supplemental Material.
"Beta-lytic metalloendopeptidase," UniProtKB, Feb. 17, 2016, accession No. A0A0S2FCI9_9GAMM, printed Mar. 12, 2019 from www.uniprot.org/uniprot/A0A0S2FCI9

* cited by examiner

[Figure 1]
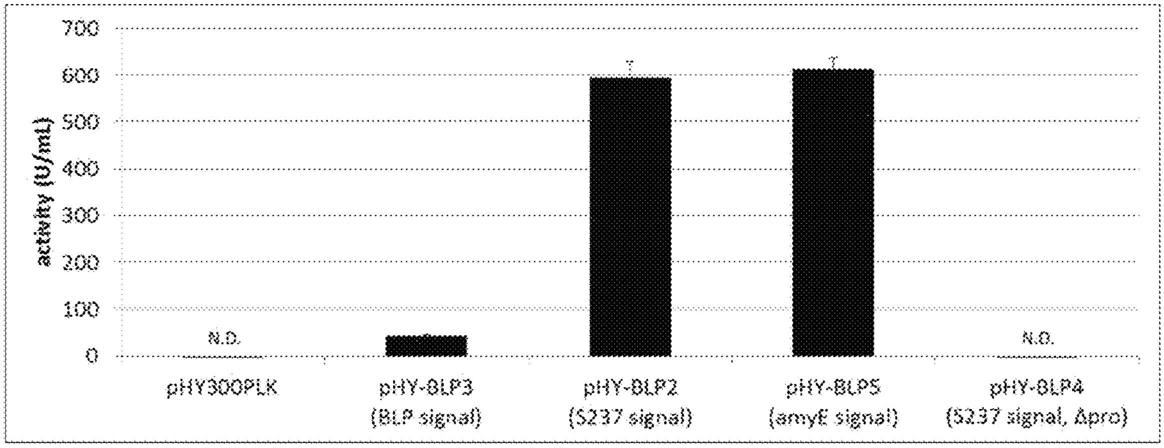
[Figure 2]
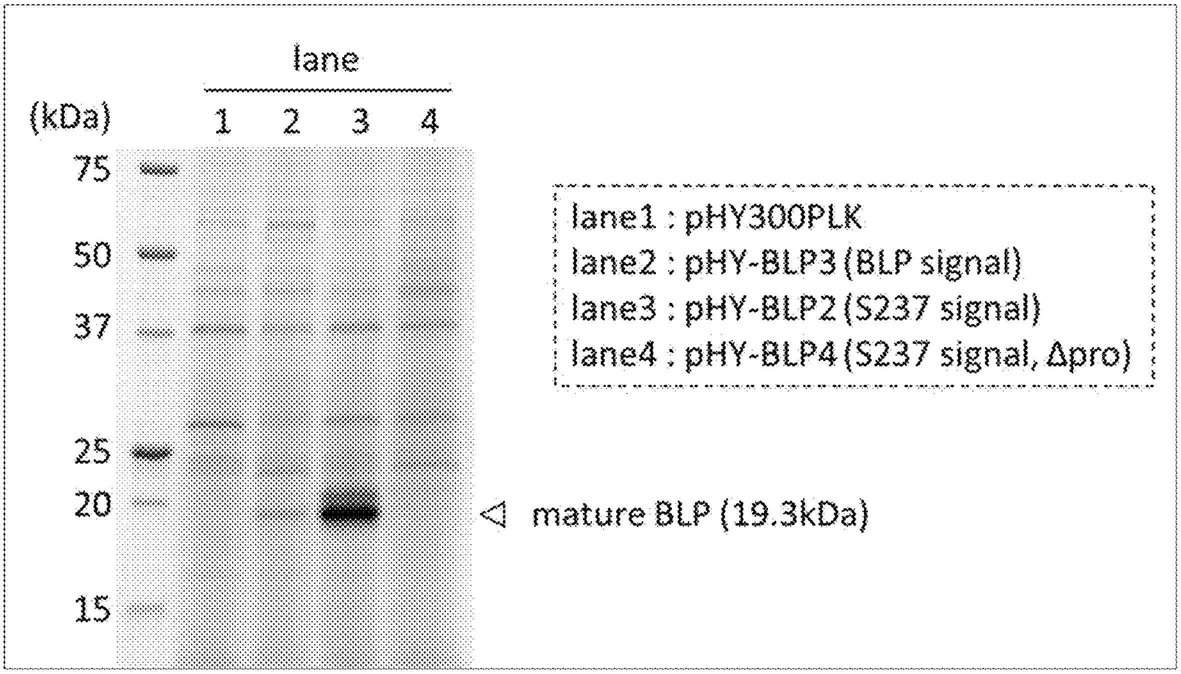

[Figure 3]
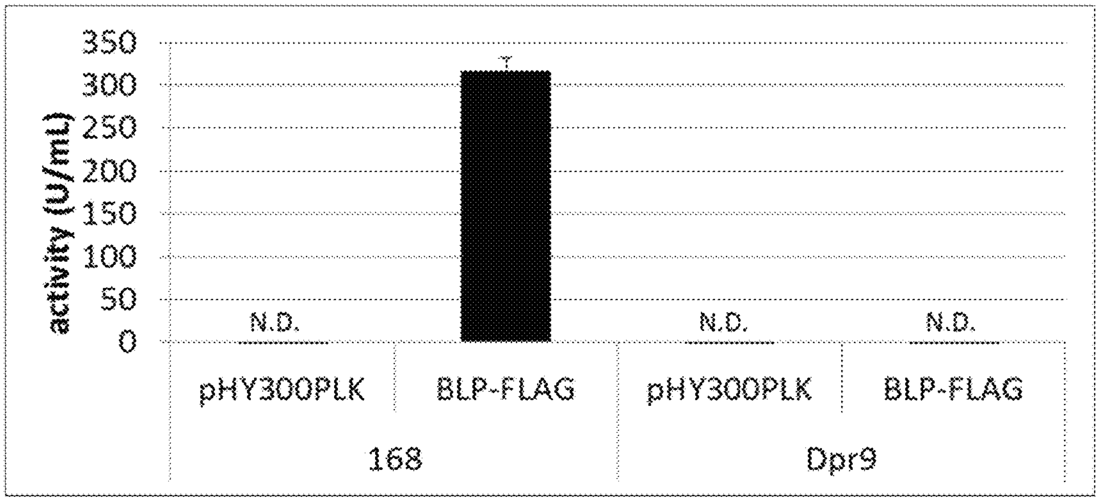
[Figure 4]
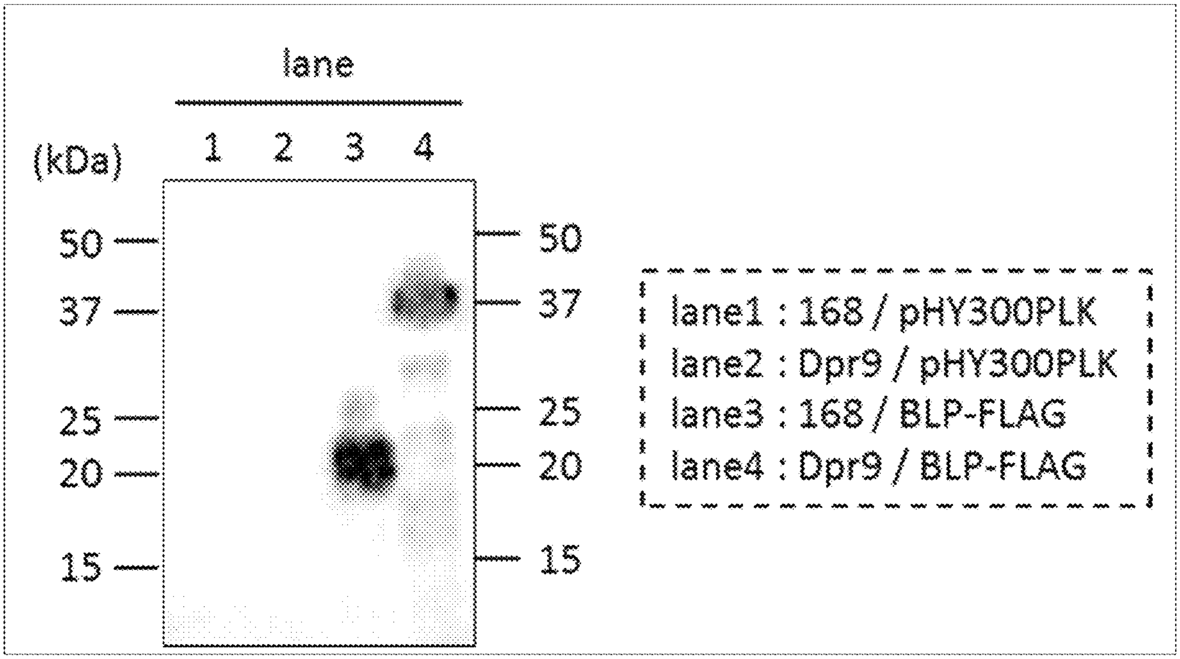

[Figure 5]
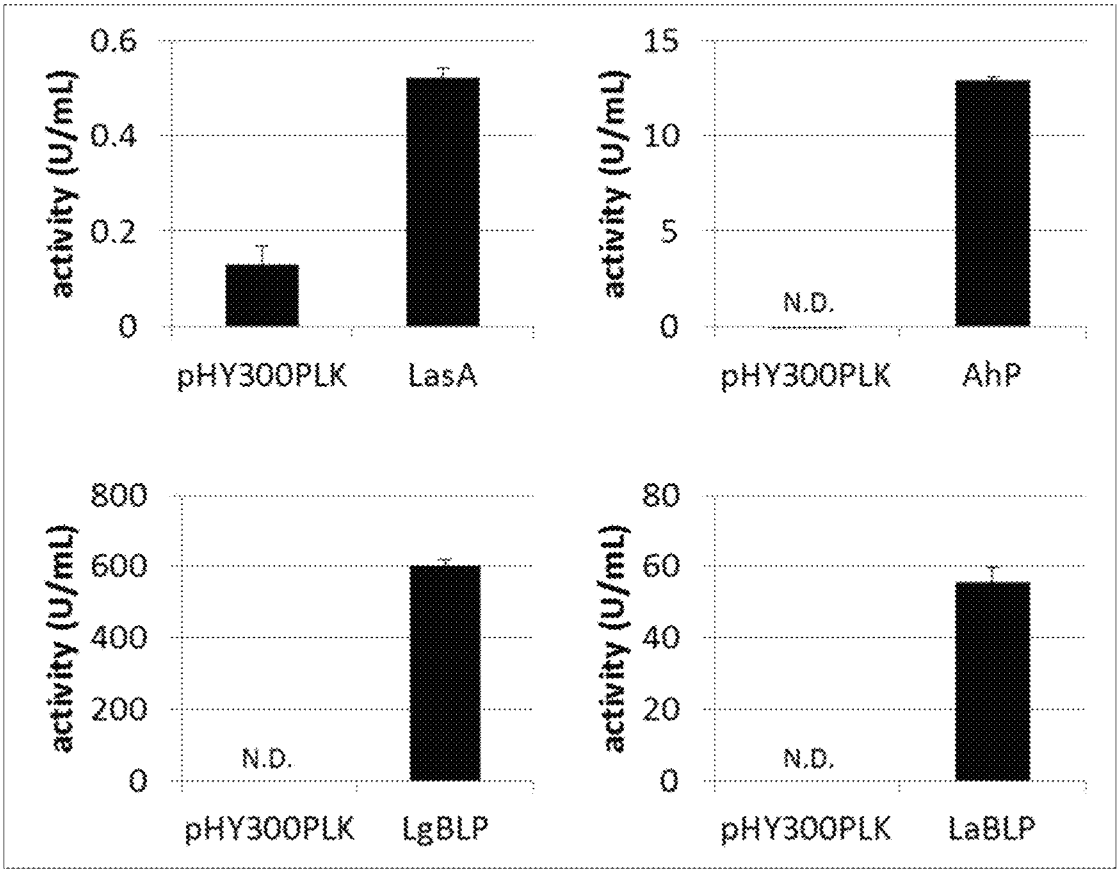

PRODUCTION METHOD FOR PROTEASE OF M23A SUBFAMILY

REFERENCE TO SEQUENCE LISTING SUBMITTED ELECTRONICALLY

The content of the electronically submitted substitute sequence listing, file name 2537 1920003 SeqListing ST25.txt, size 32,904 bytes; and date of creation Dec. 17, 2020, filed herewith, is incorporated herein by reference in its entirety.

FIELD OF THE INVENTION

The present invention relates to a method for producing an M23A family protease.

BACKGROUND OF THE INVENTION

The M23 family of proteases is a protease family defined in the MEROPS database as proteases capable of degrading Gly-Gly bonds. The M23 family proteases known also as lysis enzymes have a degrading activity of elastin or proteoglycan of bacterial cell walls are known as a bacteriolytic enzyme. The M23 family proteases are classified into two subfamilies, M23A subfamily and M23B subfamily, and each subfamily includes several types of enzymes.

In commercial production of proteins such as enzymes, a host such as *Escherichia coli* having a gene for a target protein introduced thereinto is generally cultured to express the protein, and a mature protein produced by the host is collected. In many proteases, a proprotein is first expressed, and converted into a mature protein through self-processing. The mature protein is accumulated in cells or a culture broth, and collected as a target substance. However, M23A subfamily proteases are not converted into their mature forms by self-processing, and it is impossible to collect mature proteins from *Escherichia coli* hosts (Non Patent Literatures 1 and 2). Therefore, a method of culturing a natural M23A subfamily protease-producing strain has been studied as a method for producing an M23A subfamily protease. Non Patent Literature 1 discloses a method for allowing a wild-type strain which naturally produces the M23A subfamily protease of interest to produce the M23A subfamily protease, and culture conditions which improve the protease production efficiency are further studied in order to reduce the production cost. In Non Patent Literature 3, a strain exhibiting productivity higher than existing M23A subfamily protease-producing bacteria is naturally acquired in order to reduce the production cost.

Meanwhile, Patent Literature 1 discloses a 0-lytic protease belonging to the M23A subfamily isolated from *Achromobacter lyticus* (*Achromobacter lyticus*) and discloses producing such an enzyme by allowing a host such as *Escherichia coli* or bacteria of the genus *Bacillus* to express the enzyme. However, Patent Literature 1 does not disclose producing the enzyme actually using a heterologous host. Patent Literature 1 points out the possibility of self processing of the β-lytic protease. However, as disclosed in Non Patent Literatures 1 and 2, subsequent research has reported that the M23A subfamily proteases cannot be self-processed, and therefore it is obvious that Patent Literature 1 has failed to solve the problem of lack of self-processing of the M23A subfamily proteases in the heterologous expression system. Further, as disclosed in Non Patent Literature 3, it has been reported after Patent Literature 1 that the 0-lytic protease has strong lytic activity against gram-positive bacteria such as *Bacillus subtilis*. Accordingly, the findings shown in Non Patent Literatures 1 to 3 indicate that the disclosure of Patent Literature 1 on heterologous expression of the f-lytic protease in *Escherichia coli* and bacteria of the genus *Bacillus* is not practical, and such heterologous expression is rather difficult.

As described above, mature enzymes of the M23A subfamily proteases can be obtained only by a method of culturing a natural M23A subfamily protease-producing strain due to the lack of self-processing and the lytic activity, despite their excellent characteristics.

Actually, no successful examples of heterologous expression in mature forms of the M23A subfamily proteases have been reported so far.

(Patent Literature 1) JP-A-04-108387

(Non Patent Literature 1) Molecules, 2014, 19: 4779-4790

(Non Patent Literature 2) Journal of bacteriology, 1996, 178:6608-6617

(Non Patent Literature 3) Journal of bioscience and bioengineering, 2003, 95:27-34

SUMMARY OF THE INVENTION

The present invention provides a method for producing an M23A family protease, comprising culturing bacteria of the genus *Bacillus* having a polynucleotide encoding a proprotein of the M23A family protease introduced thereinto to produce a mature form of the M23A family protease extracellularly from the bacteria of the genus *Bacillus*.

BRIEF DESCRIPTION OF DRAWINGS

FIG. 1 shows FRET-GGGGG-degrading activity in culture supernatants of recombinant *Bacillus subtilis*.

FIG. 2 shows an SDS-PAGE image of the culture supernatants of the recombinant *Bacillus subtilis*.

FIG. 3 shows FRET-GGGGG-degrading activity in culture supernatants of recombinant *Bacillus subtilis* 168 strain and Dpr9 strain.

FIG. 4 shows a Western blotting image of the culture supernatants of the recombinant *Bacillus subtilis* 168 strain and Dpr9 strain.

FIG. 5 shows FRET-GGGGG-degrading activity in culture supernatants of recombinant *Bacillus subtilis* with genes encoding proproteins of various M23A subfamily proteases introduced thereto.

DETAILED DESCRIPTION OF THE INVENTION

In this description, the identity between a nucleotide sequence and an amino acid sequence is calculated by the Lipman-Pearson method (Science, 1985, 227:1435-1441). Specifically, the identity is calculated by performing analysis using the homology analysis (Search homology) program of a genetic information processing software Genetyx-Win and setting the Unit size to compare (ktup) to 2.

In this description, "an identity of at least 80%" relating to an amino acid sequence or a nucleotide sequence means an identity of 80% or more, preferably 85% or more, more preferably 90% or more, further preferably 95% or more, further preferably 96% or more, further preferably 97% or more, further preferably 98% or more, further preferably 99% or more.

In this description, the "position corresponding to . . . " or "region corresponding to . . . " on an amino acid sequence and a nucleotide sequence can be determined by aligning a target sequence and a reference sequence (for example, the nucleotide sequence of SEQ ID NO: 1) so as to give the maximum homology to conserved amino acid residues or nucleotides present in each of the amino acid sequence or the nucleotide sequence (alignment). The alignment can be carried out using a known algorithm, and the procedure is known to those skilled in the art. For example, the alignment can be performed using the Clustal W multiple alignment program (Nucleic Acids Res., 1994, 22:4673-4680) with default settings. Alternatively, Clustal W2 and Clustal omega which are revised editions of the Clustal W can also be used therefor. The Clustal W, Clustal W2, and Clustal omega are available, for example, on a web site such as European Bioinformatics Institute (EBI [ebi.ac.uk/index-.html]) or DNA data bank of Japan (DDBJ [ddbj.nig.ac.jp/Welcome-j.html]) operated by National Institute of Genetics. The position or region of the target sequence aligned corresponding to a certain region of the reference sequence by the alignment is regarded as the "position corresponding to" or the "region corresponding to" the certain region.

In this description, "operable linkage" between a regulatory region and a gene means that the gene and the regulatory region are linked so that the gene can be expressed under the control of the regulatory region. The procedure for making the "operable linkage" between the gene and the regulatory region is known to those skilled in the art.

In this description, "upstream" and "downstream" relating to a gene refer to upstream and downstream in the transcription direction of the gene. For example, "a gene located downstream of a promoter" means that the gene is present on the 3' side of the promoter in a DNA sense strand, while the upstream of the gene means a region on the 5' side of the gene in the DNA sense strand.

In this description, the term "original" used for the functions, properties, or traits of a cell is used to express that such functions, properties, or traits are originally present in the cell. In contrast, the term "foreign" is used to express that the functions, properties, or traits are not originally present in the cell but are introduced from the outside. For example, a "foreign" gene or polynucleotide is a gene or polynucleotide introduced from the outside into the cell. The foreign gene or polynucleotide may be derived from an organism of the same species as the cell into which it is introduced or may be derived from a heterologous organism (that is, a heterologous gene or polynucleotide).

The names of the genes of *Bacillus subtilis* in this description are described based on the *Bacillus subtilis* genome data published on the internet ([bacillus.genome.ad.jp/], updated on Jan. 18, 2006) by JAFAN: Japan Functional Analysis Network for *Bacillus subtilis* (BSORF DB). The gene numbers of *Bacillus subtilis* in this description represent gene numbers registered in the BSORF DB.

The present invention provides a method for producing an M23A family protease.

The present inventors surprisingly found that a mature form of the M23A family protease can be efficiently collected from a culture broth by introducing an M23A family protease gene into a *Bacillus* host and culturing it, in contrast to the conventional finding that an M23A subfamily protease is not converted into a mature form in a heterologous host (for example, Non Patent Literatures 1 and 2).

The M23A subfamily protease has detergency for corneum-derived stain in addition to the activity of degrading elastin or bacterial cell walls and is thus expected to have various industrial applications due to its excellent characteristics (Japanese Patent Application No. 2018-005193). The method of the present invention enables a mature form of the M23A family protease to be efficiently produced with a simple procedure using a *Bacillus* host. The present invention can overcome the problems in the conventional M23A family protease production such as low productivity in a wild-type strain naturally expressing a mature form of the M23A family protease and lack of the mature form in an *Escherichia coli* host.

The method for producing an M23A subfamily protease of the present invention includes culturing bacteria of the genus *Bacillus* having a polynucleotide encoding a proprotein of the target M23A subfamily protease introduced thereinto.

The M23A subfamily protease produced according to the present invention is a mature enzyme having an activity of degrading glycine-glycine bonds in a peptide sequence. Preferable examples of the M23A subfamily protease produced according to the present invention include β-lytic metalloprotease (beta-lytic metallopeptidase; BLP), LasA protein (LasA, which is referred to also as Staphylolysin), and *Aeromonas hydrophila* proteinase (AhP, which is referred to also as Mername-AA291 peptidase). These are disclosed in the MEROPS database (merops.sanger.ac.uk) as proteases belonging to the M23A subfamily. BLP (MEROPS ID: M23.001) is a polypeptide consisting of the amino acid sequence of SEQ ID NO: 1. LasA (MEROPS ID: M23.002) is a polypeptide consisting of the amino acid sequence of SEQ ID NO: 4. AhP (MEROPS ID: M23.003) is a polypeptide consisting of the amino acid sequence of SEQ ID NO: 7. BLP, LasA, and AhP are enzymes having an activity of degrading glycine-glycine bonds in peptide sequences.

Other preferable examples of the M23A subfamily protease produced according to the present invention include a polypeptide having functions equivalent to BLP, LasA, and AhP described above. Examples of the polypeptide having functions equivalent to BLP, LasA, and AhP include a polypeptide which consists of an amino acid sequence having an identity of at least 80% with any one of the amino acid sequences of SEQ ID NOs: 1, 4, and 7 and which has an activity of degrading glycine-glycine bonds in a peptide sequence. Preferable examples of the polypeptide having functions equivalent to BLP include a polypeptide which consists of an amino acid sequence having an identity of at least 80% with the amino acid sequence of SEQ ID NO: 1, preferably an amino acid sequence having His at the positions corresponding to positions 22, 121, and 123 and Asp at the position corresponding to position 36 in the amino acid sequence of SEQ ID NO: 1 and which has an activity of degrading glycine-glycine bonds in a peptide sequence. Preferable examples of the polypeptide having functions equivalent to LasA include a polypeptide which consists of an amino acid sequence having an identity of at least 80% with the amino acid sequence of SEQ ID NO: 4, preferably an amino acid sequence having His at the positions corresponding to positions 23, 120, and 122 and Asp at the position corresponding to position 36 in the amino acid sequence of SEQ ID NO: 4 and which has an activity of degrading glycine-glycine bonds in a peptide sequence. Preferable examples of the polypeptide having functions equivalent to AhP include a polypeptide which consists of an amino acid sequence having an identity of at least 80% with the amino acid sequence of SEQ ID NO: 7, preferably an amino acid sequence having His at the positions corresponding to positions 21, 118, and 120 and Asp at the position corresponding to position 34 in the amino acid sequence of SEQ ID NO: 7 and which has an activity of degrading glycine-glycine bonds in a peptide sequence.

Still other preferable examples of the M23A subfamily protease produced according to the present invention include BLP homolog derived from *Lysobacter gummosus* (WP 057941690.1, which will be hereinafter referred to as LgBLP in this description), and BLP homolog derived from *Lysobacter antibioticus* (WP 057970430.1, which will be hereinafter referred to as LaBLP in this description). LgBLP is a polypeptide consisting of the amino acid sequence of SEQ ID NO: 10. LaBLP is a polypeptide consisting of the amino acid sequence of SEQ ID NO: 13. LgBLP and LaBLP are enzymes having an activity of degrading glycine-glycine bonds in peptide sequences.

Still other preferable examples of the M23A subfamily protease produced according to the present invention include a polypeptide having functions equivalent to LgBLP and LaBLP described above. Preferable examples of the polypeptide having functions equivalent to LgBLP include a polypeptide which consists of an amino acid sequence having an identity of at least 80% with the amino acid sequence of SEQ ID NO: 10 and which has an activity of degrading glycine-glycine bonds in a peptide sequence. Preferable examples of the polypeptide having functions equivalent to LaBLP include a polypeptide which consists of an amino acid sequence having an identity of at least 80% with the amino acid sequence of SEQ ID NO: 13 and which has an activity of degrading glycine-glycine bonds in a peptide sequence.

Preferably, the M23A subfamily protease produced according to the present invention is at least one selected from the group consisting of BLP, LasA, AhP, LgBLP, LaBLP, and the polypeptide having functions equivalent thereto described above.

The polynucleotide encoding a proprotein of the M23A subfamily protease, which is introduced into bacteria of the genus *Bacillus* to be used in the present invention, is a polynucleotide containing a sequence encoding a proregion of a target M23A subfamily protease produced according to the method of the present invention and a sequence encoding its mature protein. The proregion of the M23A subfamily protease is a region which contributes to formation of the three-dimensional structure of a mature protein region of the M23A subfamily protease located downstream of the proregion on the proprotein. Examples of the polynucleotide encoding the proprotein include a polynucleotide encoding a proprotein of BLP (SEQ ID NO: 2), a polynucleotide encoding a proprotein of LasA (SEQ ID NO: 5), a polynucleotide encoding a proprotein of AhP (SEQ ID NO: 8), a polynucleotide encoding a proprotein of LgBLP (SEQ ID NO: 11), and a polynucleotide encoding a proprotein of LaBLP (SEQ ID NO: 14). Other examples of the polynucleotide encoding the proprotein include a polynucleotide encoding a proprotein of BLP containing a secretion signal (SEQ ID NO: 3), a polynucleotide encoding a proprotein of LasA containing a secretion signal (SEQ ID NO: 6), a polynucleotide encoding a proprotein of AhP containing a secretion signal (SEQ ID NO: 9), a polynucleotide encoding a proprotein of LgBLP containing a secretion signal (SEQ ID NO: 12), and a polynucleotide encoding a proprotein of LaBLP containing a secretion signal (SEQ ID NO: 15).

In the polynucleotide of SEQ ID NO: 2, the nucleotide region at positions 523 to 1062 encodes the mature protein of BLP, and the upstream region thereof encodes the proregion. In the polynucleotide of SEQ ID NO: 3, the nucleotide region at positions 595 to 1134 encodes the mature protein of BLP, a region encoding the proregion is located upstream thereof, and the further upstream thereof encodes the secretion signal. The region encoding the secretion signal can be determined using a tool such as SignalP (cbs.dtu.dk/services/SignalP/). The secretion signal coding region of BLP on the polynucleotide of SEQ ID NO: 3 based on the prediction by SignalP is the nucleotide region at positions 1 to 72.

In the polynucleotide of SEQ ID NO: 5, the nucleotide region at positions 616 to 1164 encodes the mature protein of LasA, and the upstream thereof encodes the proregion. In the polynucleotide of SEQ ID NO: 6, the nucleotide region at positions 709 to 1257 encodes the mature protein of LasA, a region encoding the proregion is located upstream thereof, and the further upstream thereof encodes the secretion signal. The secretion signal coding region of LasA on the polynucleotide of SEQ ID NO: 6 based on the prediction by SignalP is the nucleotide region at positions 1 to 93.

In the polynucleotide of SEQ ID NO: 8, the nucleotide region at positions 565 to 1104 encodes the mature protein of AhP, and the upstream thereof encodes the proregion. In the polynucleotide of SEQ ID NO: 9, the nucleotide region at positions 625 to 1164 encodes the mature protein of AhP, a region encoding the proregion is located upstream thereof, and the further upstream thereof encodes the secretion signal. The secretion signal coding region of AhP on the polynucleotide of SEQ ID NO: 9 based on the prediction by SignalP is the nucleotide region at positions 1 to 60.

In the polynucleotide of SEQ ID NO: 11, the nucleotide region at positions 529 to 1065 encodes the mature protein of LgBLP, and the upstream thereof encodes the proregion. In the polynucleotide of SEQ ID NO: 12, the nucleotide region at positions 628 to 1164 encodes the mature protein of LgBLP, a region encoding the proregion is located upstream thereof, and the further upstream thereof encodes the secretion signal. The secretion signal coding region of LgBLP on the polynucleotide of SEQ ID NO: 12 based on the prediction by SignalP is the nucleotide region at positions 1 to 99.

In the polynucleotide of SEQ ID NO: 14, the nucleotide region at positions 550 to 1086 encodes the mature protein of LaBLP, and the upstream thereof encodes the proregion. In the polynucleotide of SEQ ID NO: 15, the nucleotide region at positions 628 to 1164 encodes the mature protein of LaBLP, a region encoding the proregion is located upstream thereof, and the further upstream thereof encodes the secretion signal. The secretion signal coding region of LaBLP on the polynucleotide of SEQ ID NO: 15 based on the prediction by SignalP is the nucleotide region at positions 1 to 78.

The proregion encoded by such a polynucleotide contributes to formation of the three-dimensional structure of the mature protein region located downstream thereof.

Accordingly, further examples of the polynucleotide encoding a proprotein of the target M23A subfamily protease include a polynucleotide containing a polynucleotide encoding a proregion of the M23A subfamily protease and a polynucleotide encoding a mature protein of the M23A subfamily protease linked downstream thereof. Examples of the polynucleotide encoding the proregion of the M23A subfamily protease include a polynucleotide consisting of the sequence of the nucleotide region at positions 1 to 522 in SEQ ID NO: 2, the sequence of the nucleotide region at positions 1 to 615 in SEQ ID NO: 5, the sequence of the nucleotide region at positions 1 to 564 in SEQ ID NO: 8, the sequence of the nucleotide region at positions 1 to 528 in SEQ ID NO: 11, the sequence of the nucleotide region at positions 1 to 549 in SEQ ID NO: 14, or a sequence having an identity of at least 80% identical therewith. The proregion encoded by such a polynucleotide contributes to formation of the three-dimensional structure of the mature protein region of the M23A subfamily protease located downstream thereof. Examples of the polynucleotide encoding the mature protein of the M23A subfamily protease include polynucleotides encoding BLP, LasA, AhP, LgBLP, LaBLP, and the polypeptide having functions equivalent thereto described above.

Further examples of the polynucleotide encoding the proprotein of the target M23A subfamily protease include:

a polynucleotide which consists of a nucleotide sequence having an identity of at least 80% with the nucleotide sequence of SEQ ID NO: 2 and contains a nucleotide sequence encoding BLP, LasA, AhP, LgBLP, LaBLP, or a polypeptide having functions equivalent thereto (preferably, BLP or a polypeptide having functions equivalent thereto) in a region corresponding to the nucleotide region at positions 523 to 1062 in SEQ ID NO: 2;

a polynucleotide which contains the sequence of the nucleotide region at positions 1 to 522 in SEQ ID NO: 2 or a sequence having an identity of at least 80% therewith and encoding a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably BLP or a polypeptide having functions equivalent thereto);

a polynucleotide which consists of a nucleotide sequence having an identity of at least 80% with the nucleotide sequence of SEQ ID NO: 3 and contains a nucleotide sequence encoding BLP, LasA, AhP, LgBLP, LaBLP, or a polypeptide having functions equivalent thereto (preferably, BLP or a polypeptide having functions equivalent thereto) in a region corresponding to the nucleotide region at positions 595 to 1134 in SEQ ID NO: 3;

a polynucleotide which contains the sequence of the nucleotide region at positions 1 to 594 in SEQ ID NO: 3 or a sequence having an identity of at least 80% therewith and encoding a secretion signal and a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably BLP or a polypeptide having functions equivalent thereto);

a polynucleotide which consists of a nucleotide sequence having an identity of at least 80% with the nucleotide sequence of SEQ ID NO: 5 and contains a nucleotide sequence encoding BLP, LasA, AhP, LgBLP, LaBLP, or a polypeptide having functions equivalent thereto (preferably LasA or a polypeptide having functions equivalent thereto) in a region corresponding to the nucleotide region at positions 616 to 1164 in SEQ ID NO: 5;

a polynucleotide which contains the sequence of the nucleotide region at positions 1 to 615 in SEQ ID NO: 5 or a sequence having an identity of at least 80% therewith and encoding a proregion of the M23A subfamily protease and contains a sequence encoding a mature protein of the M23A subfamily protease linked downstream thereof (BLP, LasA, AhP, LgBLP, LaBLP, or polypeptides having functions equivalent thereto, preferably LasA or a polypeptide having functions equivalent thereto);

a polynucleotide which consists of a nucleotide sequence having an identity of at least 80% identical with the nucleotide sequence of SEQ ID NO: 6 and contains a nucleotide sequence encoding BLP, LasA, AhP, LgBLP, LaBLP, or a polypeptide having functions equivalent thereto (preferably, LasA or a polypeptide having functions equivalent thereto) in a region corresponding to the nucleotide region at positions 709 to 1257 in SEQ ID NO: 6;

a polynucleotide which contains the sequence of the nucleotide region at positions 1 to 708 in SEQ ID NO: 6 or a sequence having an identity of at least 80% therewith and encoding a secretion signal and a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably LasA or a polypeptide having functions equivalent thereto);

a polynucleotide which consists of a nucleotide sequence having an identity of at least 80% with the nucleotide sequence of SEQ ID NO: 8 and contains a nucleotide sequence encoding BLP, LasA, AhP, LgBLP, LaBLP, or a polypeptide having functions equivalent thereto (preferably, AhP or a polypeptide having functions equivalent thereto) in a region corresponding to the nucleotide region at positions 565 to 1104 in SEQ ID NO: 8;

a polynucleotide which contains the sequence of the nucleotide region at positions 1 to 564 in SEQ ID NO: 8 or a sequence having an identity of at least 80% therewith and encoding a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably AhP or a polypeptide having functions equivalent thereto);

a polynucleotide which consists of a nucleotide sequence having an identity of at least 80% identical with the nucleotide sequence of SEQ ID NO: 9 and contains a nucleotide sequence encoding BLP, LasA, AhP, LgBLP, LaBLP, or a polypeptide having functions equivalent thereto (preferably, AhP or a polypeptide having functions equivalent thereto) in a region corresponding to the nucleotide region at positions 625 to 1164 in SEQ ID NO: 9;

a polynucleotide which contains the sequence of the nucleotide region at positions 1 to 624 in SEQ ID NO: 9 or a sequence having an identity of at least 80% therewith and encoding a secretion signal and a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably AhP or a polypeptide having functions equivalent thereto);

a polynucleotide which consists of a nucleotide sequence having an identity of at least 80% with the nucleotide sequence of SEQ ID NO: 11 and contains a nucleotide sequence encoding BLP, LasA, AhP, LgBLP, LaBLP, or a polypeptide having functions equivalent thereto (preferably, LgBLP or a polypeptide having functions equivalent thereto) in a region corresponding to the nucleotide region at positions 529 to 1065 in SEQ ID NO: 11;

a polynucleotide which contains the sequence of the nucleotide region at positions 1 to 528 in SEQ ID NO: 11 or a sequence having an identity of at least 80% there and encoding a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably LgBLP or a polypeptide having functions equivalent thereto);

a polynucleotide which consists of a nucleotide sequence having an identity of at least 80% with the nucleotide sequence of SEQ ID NO: 12 and contains a nucleotide sequence encoding BLP, LasA, AhP, LgBLP, LaBLP, or a polypeptide having functions equivalent thereto (preferably, LgBLP or a polypeptide having functions equivalent thereto) in a region corresponding to the nucleotide region at positions 628 to 1164 in SEQ ID NO: 12;

a polynucleotide which contains the sequence of the nucleotide region at positions 1 to 627 in SEQ ID NO: 12 or a sequence having an identity of at least 80% there and encoding a secretion signal and a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably LgBLP or a polypeptide having functions equivalent thereto);

a polynucleotide which consists of a nucleotide sequence having an identity of at least 80% with the nucleotide sequence of SEQ ID NO: 14 and contains a nucleotide sequence encoding BLP, LasA, AhP, LgBLP, LaBLP, or a polypeptide having functions equivalent thereto (preferably, LaBLP or a polypeptide having functions equivalent thereto) in a region corresponding to the nucleotide region at positions 550 to 1086 in SEQ ID NO: 14;

a polynucleotide which contains the sequence of the nucleotide region at positions 1 to 549 in SEQ ID NO: 14 or a sequence having an identity of at least 80% therewith and encoding a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably LaBLP or a polypeptide having functions equivalent thereto); a polynucleotide which consists of a nucleotide sequence having an identity of at least 80% with the nucleotide sequence of SEQ ID NO: 15 and contains a nucleotide sequence encoding BLP, LasA, AhP, LgBLP, LaBLP, or a polypeptide having functions equivalent thereto (preferably, LaBLP or a polypeptide having functions equivalent thereto) in a region corresponding to the nucleotide region at positions 628 to 1164 in SEQ ID NO: 15; and a polynucleotide which contains the sequence of the nucleotide region at positions 1 to 627 in SEQ ID NO: 15 or a sequence having an identity of at least 80% therewith and encoding a secretion signal and a proregion of the M23A subfamily protease and contains a sequence encoding a mature protein of the M23A subfamily protease linked downstream thereof (BLP, LasA, AhP, LgBLP, LaBLP, or a polypeptide having functions equivalent thereto, preferably LaBLP or a polypeptide having functions equivalent thereto).

Examples of the nucleotide sequence encoding BLP, LasA, AhP, LgBLP, and LaBLP, and polypeptides having functions equivalent thereto contained in the polynucleotide include the sequence 523 to 1062 of SEQ ID NO: 2, the sequence 616 to 1164 of SEQ ID NO: 5, the sequence 565 to 1104 of SEQ ID NO: 8, the sequence 529 to 1065 of SEQ ID NO: 11, and the sequence 550 to 1086 of SEQ ID NO: 14, and a nucleotide sequence having an identity of at least 80% with any one of them. The polypeptides encoded by these nucleotide sequences all have an activity of degrading glycine-glycine bonds in a peptide sequence.

The polynucleotide encoding the proprotein can be prepared by a usual method. For example, the polynucleotide encoding the proprotein can be prepared by extracting genomic DNA from microorganisms which originally produce the target M23A subfamily protease by a usual method or extracting RNA to synthesize cDNA by reverse transcription. For example, the polynucleotide encoding a proprotein of BLP (SEQ ID NOs: 2 and 3) can be prepared from *Lysobacter* sp. (NBRC 12725 or NBRC 12726), *Achromobacter lyticus* M497-1, *Lysobacter* sp. IB-9374, *Lysobacter gummosus* DSMZ 6980, or the like. The polynucleotide encoding a proprotein of LasA (SEQ ID NOs: 5 and 6) can be prepared from *Pseudomonas aeruginosa* PA01, *Pseudomonas aeruginosa* ATCC 10145, *Pseudomonas aeruginosa* FRD1, or the like. The polynucleotide encoding a proprotein of AhP (SEQ ID NOs: 8 and 9) can be prepared from *Aeromonas hydrophila* subsp. *hydrophila* ATCC 7966, *Aeromonas hydrophila* (Chester) Stanier (ATCC 51307), or the like. The polynucleotide encoding a proprotein of LgBLP (SEQ ID NOs: 11 and 12) can be prepared from *Lysobacter gummosus*, or the like. The polynucleotide encoding a proprotein of LaBLP (SEQ ID NOs: 14 and 15) can be prepared from *Lysobacter antibioticus*, or the like. The aforementioned microorganisms can be purchased from public culture collections.

The polynucleotide encoding a proprotein of the target M23A subfamily protease may be prepared by further performing site-directed mutagenesis on the polynucleotide encoding the proprotein obtained by the aforementioned procedure. Alternatively, the polynucleotide encoding a proprotein of the target M23A subfamily protease may be chemically synthesized based on the amino acid sequence of the proprotein.

The polynucleotide encoding the proprotein may be operably linked to the regulatory region. In this description, the "regulatory region" is a region having a function to control the expression of a gene located downstream thereof in a cell, preferably having a function to constitutively express or highly express the gene located downstream thereof. More specifically, the regulatory region can be defined as a region present upstream of a coding region of a gene and having a function to control the transcription of the coding region by interaction of RNA polymerase. Preferably, the regulatory region in this description means a region of about 200 to 600 nucleotides located upstream of the coding region of the gene. The regulatory region includes the transcription initiation regulatory region and/or the translation initiation regulatory region, or a region ranging from the transcription initiation regulatory region to the translation initiation regulatory region. The transcription initiation regulatory region is a region including the promoter and the transcription initiation point, and the translation initiation regulatory region is a site corresponding to the Shine-Dalgarno (SD) sequence forming the ribosome-binding site together with the start codon (Shine, J., Dalgarno, L., Proc. Natl. Acad. Sci. USA., 1974, 71:1342-1346).

Preferable examples of the regulatory region include regulatory regions which function in bacteria of the genus *Bacillus*, such as the regulatory region of α-amylase gene, protease gene, aprE gene, or spoVG gene derived from bacteria of the genus *Bacillus*, the regulatory region of the cellulase gene of *Bacillus* sp. KSM-S237 strain (JP-A-2000-210081), the regulatory region of the cellulase gene of *Bacillus* sp. KSM-64 strain (JP-A-2011-10387), and the regulatory region of kanamycin resistance gene or chloramphenicol resistance gene derived from *Staphylococcus aureus* (for both genes, refer to JP-A-2009-089708), but there is no specific limitation thereto. More preferable examples of the regulatory region include the promoter of the cellulase gene of *Bacillus* sp. KSM-S237 strain (SEQ ID NO: 16) and the promoter of the cellulase gene of *Bacillus* sp. KSM-64 strain (SEQ ID NO: 17). Further, preferable examples of the regulatory region include a nucleotide sequence having an identity of at least 80% with SEQ ID NO: 16 or 17 and having a function to control the transcription and translation of a gene.

The polynucleotide encoding the proprotein may be operably linked to a sequence encoding a secretion signal having a function to secrete the protein expressed extracellularly (referred to as a secretion signal sequence). Preferable examples of the secretion signal sequence include a secretion signal sequence which functions in bacteria of the genus *Bacillus*, such as a secretion signal sequence derived from bacteria of the genus *Bacillus*. Preferable examples of the secretion signal sequence derived from bacteria of the genus *Bacillus* include the secretion signal sequence of the cellulase gene of *Bacillus* sp. KSM-S237 strain (SEQ ID NO: 18), the secretion signal sequence of the cellulase gene of *Bacillus* sp. KSM-64 strain (SEQ ID NO: 19), and the secretion signal sequence of *Bacillus subtilis* amylase gene amyE (SEQ ID NO: 20). Further examples of the secretion signal sequence derived from bacteria of the genus *Bacillus* include a nucleotide sequence having an identity of at least 80% with any one of SEQ ID NOs: 18 to 20 and having a function to secrete the protein expressed extracellularly. The sequence encoding the proprotein to be linked to the secretion signal sequence derived from bacteria of the genus *Bacillus* may contain or not contain the secretion signal sequence of a natural M23A subfamily protease (for example, the secretion signal sequence contained in SEQ ID NOs: 3, 6, 9, 12, or 15 described above).

Accordingly, the polynucleotide encoding the proprotein may contain a nucleotide sequence of the untranslated region (UTR) in addition to the open reading frame (ORF). For example, the polynucleotide may contain the promoter, the secretion signal sequence, and the terminator described above.

The polynucleotide encoding the proprotein can be introduced into bacteria of the genus *Bacillus* by a usual method. For example, the polynucleotide encoding the proprotein or a vector containing the polynucleotide can be introduced into host *Bacillus* cells to incorporate the polynucleotide into the genome of the host cells. Alternatively, an expression vector containing the polynucleotide may be introduced into the host *Bacillus* cells.

For introducing the polynucleotide or the vector into the host *Bacillus* cells, known transformation techniques such as a competent cell method, an electroporation method, a protoplast method, a particle gun method, and a PEG method can be applied, for example.

The vector containing the polynucleotide encoding the proprotein can be constructed by inserting into and linking to any vector the polynucleotide encoding the proprotein and, as required, the regulatory region or the secretion signal sequence by a usual method. The type of the vector is not specifically limited and may be any vector such as a plasmid, phage, phagemid, cosmid, virus, YAC vector, and shuttle vector. The vector is preferably a vector which can be amplified within a host cell, more preferably an expression vector. Preferable examples of the vector include, but is not limited to: a shuttle vector such as pHA3040SP64, pHSP64R, or pASP64 (JP-B-3492935), and pHY300PLK (expression vectors capable of transforming both of *Escherichia coli* and *Bacillus subtilis*; Jpn J Genet, 1985, 60:235-243), pAC3 (Nucleic Acids Res, 1988, 16:8732); and a plasmid which can be used for transforming bacteria of the genus *Bacillus* such as pUB110 (J Bacteriol, 1978, 134:318-329), and pTA10607 (Plasmid, 1987, 18:8-15). Further, a plasmid derived from *Escherichia coli* (for example, pET22b(+), pBR322, pBR325, pUC57, pUC118, pUC119, pUC18, pUC19, and pBluescript) also can be used.

The bacteria of the genus *Bacillus* to have the polynucleotide encoding the proprotein introduced thereinto is not particularly limited, and is preferably *Bacillus subtilis* or mutant strains thereof. Preferably, the bacteria of the genus *Bacillus* extracellularly secrete a protease other than the target M23A subfamily protease or releases the proteases with lysis of the bacteria (this process will be hereinafter referred to simply as "release"). Examples of the other protease include at least one selected from the group consisting of extracellular proteases encoded by aprE, epr, wprA, mpr, nprB, bpr, nprE, vpr, aprX, and a gene corresponding thereto. Conventionally, such an extracellular protease is known to cause a reduction in productivity of a recombinant enzyme, and it has been also reported that the productivity of a recombinant enzyme was improved in a *Bacillus subtilis* strain lacking such an extracellular protease (JP-A-2006-174707). In contrast, in the method for producing an M23A family protease according to the present invention, bacteria of the genus *Bacillus* holding such an extracellular protease are rather preferably used as a host for enzyme production.

These aprE, epr, wprA, mpr, nprB, bpr, nprE, vpr, and aprX are *Bacillus subtilis* genes. Table 1 shows the gene numbers of these genes and the functions of proteins to be encoded. Examples of the genes corresponding to aprE, epr, wprA, mpr, nprB, bpr, nprE, vpr, and aprX include genes derived from bacteria of the genus *Bacillus* having an identity of at least 80% respectively with epr, wprA, mpr, nprB, bpr, nprE, vpr, and aprX in the nucleotide sequence and encoding proteins having the same functions (shown in Table 1). These genes can be searched for in the BSORF DB.

TABLE 1

| Gene name | Gene number in BSORF DB | Function of protein encoded |
|---|---|---|
| aprE | BG10190 | Serine alkaline protease (subtilisin E) |
| epr | BG10561 | Minor extracellular serine protease |
| wprA | BG11846 | Cell wall-bound protease precursor (CWBP23, CWBP52) |
| mpr | BG10690 | Extracellular metalloprotease |
| nprB | BG10691 | Extracellular neutral protease B |
| bpr | BG10233 | Bacillopeptidase F |
| nprE | BG10448 | Extracellular neutral metalloprotease |
| vpr | BG10591 | Minor extracellular serine protease |
| aprX | BG12567 | Intracellular serine protease (released extracellularly) |

Accordingly, the bacteria of the genus *Bacillus* to have the polynucleotide encoding the proprotein introduced thereinto preferably has an extracellular protease activity. The extracellular protease activity of microorganisms can be detected by measuring the azocasein-degrading activity of the culture supernatant of the microorganisms, and the azocasein-degrading activity of the culture supernatant can be measured by the method shown in Example 5 (5-2), which will be described below. The microorganisms whose culture supernatant has the azocasein-degrading activity are determined to have the extracellular protease activity.

Preferably, the bacteria of the genus *Bacillus* having the polynucleotide encoding the proprotein introduced thereinto is *Bacillus subtilis* or a mutant strain thereof which expresses at least one gene selected from the group consisting of aprE or a gene corresponding thereto, epr or a gene corresponding thereto, wprA or a gene corresponding thereto, mpr or a gene corresponding thereto, nprB or a gene corresponding thereto, bpr or a gene corresponding thereto, nprE or a gene corresponding thereto, vpr or a gene corresponding thereto, and aprX or a gene corresponding thereto, and which secretes or releases the extracellular protease encoded by each of the genes extracellularly. More preferably, the bacteria of the genus *Bacillus* is *Bacillus subtilis* or a mutant strain thereof which expresses aprE or a gene corresponding thereto, epr or a gene corresponding thereto, wprA or a gene corresponding thereto, mpr or a gene corresponding thereto, nprB or a gene corresponding thereto, bpr or a gene corresponding thereto, nprE or a gene corresponding thereto, vpr or a gene corresponding thereto, and aprX or a gene corresponding thereto, and which secretes or releases the extracellular protease encoded by each of the genes extracellularly.

In the method of the present invention, recombinant bacteria of the genus *Bacillus* having the polynucleotide encoding a proprotein of the target M23A subfamily protease introduced thereinto and obtained by the procedure as described above is cultured. The bacteria of the genus *Bacillus* may be cultured according to a common method for culturing bacteria of the genus *Bacillus*. For example, the culture medium for bacteria of the genus *Bacillus* contains a carbon source and a nitrogen source necessary for the growth of the bacteria. Examples of the carbon source include glucose, dextran, soluble starch, sucrose, and methanol. Examples of the nitrogen source include an ammonium salt, nitrate, amino acid, corn steep liquor, peptone, casein, meat extract, soybean meal, and potato extract. As required, the culture medium may contain other nutrients, such as an inorganic salt (for example, sodium chloride, calcium chloride, sodium dihydrogen phosphate, and magnesium chloride), vitamin, and antibiotic (for example, tetracycline, neomycin, kanamycin, spectinomycin, and erythromycin). The culture conditions, such as temperature, aeration and stirring conditions, pH of the culture medium, and culture time can be appropriately selected corresponding to the type, traits, culture scale, and the like of the bacteria.

In the method of the present invention, the proprotein of the target M23A subfamily protease is expressed by culturing the recombinant bacteria of the genus *Bacillus* as above. The proprotein expressed is secreted or released extracellularly and processed there due to the action of other extracellular proteases secreted or released by the bacteria of the genus *Bacillus* to be converted into a mature form of the M23A subfamily protease having an enzymatic activity. Accordingly, the mature form of the M23A family protease is produced extracellularly from the recombinant bacteria of the genus *Bacillus* in the method of the present invention. The mature form of the M23A subfamily protease produced accumulates in the extracellular components of the culture broth.

By the above procedure, the mature form of the M23A subfamily protease is produced according to the method of the present invention. The M23A subfamily protease produced can be collected from the culture broth according to a conventional method. In the method of the present invention, the M23A subfamily protease produced extracellularly accumulates, and therefore the target enzyme can be collected without destroying the cells. For example, the enzyme can be collected by a general method such as removing the cells from the culture broth by centrifugation, filtration, or the like, followed by precipitation using a salt such as ammonium sulfate or an organic solvent such as ethanol, concentration or desalination using an ultrafiltration membrane or the like, and purification using various chromatography such as ion exchange or gel filtration, from the supernatant or filtrate collected.

The present invention further includes the following materials, production methods, applications, and methods as illustrative embodiments. However, the present invention is not limited to these embodiments.

[1] A method for producing an M23A family protease, comprising culturing bacteria of the genus *Bacillus* having a polynucleotide encoding a proprotein of the M23A family protease introduced thereinto to produce a mature form of the M23A family protease extracellularly from the bacteria of the genus *Bacillus*.

[2] The method according to [1], wherein the M23A family protease is preferably:

a polypeptide consisting of the amino acid sequence of SEQ ID NO: 1, 4, 7, 10, or 13; or a polypeptide which consists of an amino acid sequence having an identity of at least 80% with the amino acid sequence of any one of SEQ ID NOs: 1, 4, 7, 10, and 13 and has an activity of degrading glycine-glycine bonds in a peptide sequence.

[3] The method according to [2], wherein the polynucleotide encoding a proprotein of the M23A family protease is preferably:

a polynucleotide consisting of the nucleotide sequence of any one of SEQ ID NOs: 2, 3, 5, 6, 8, 9, 11, 12, 14, and 15; or a polynucleotide comprising a polynucleotide encoding a proregion of the M23A subfamily protease and a polynucleotide encoding the M23A subfamily protease linked downstream thereof, and wherein the polynucleotide encoding a proregion of an M23A subfamily protease is preferably a polynucleotide which consists of the sequence of the nucleotide region at positions 1 to 522 in SEQ ID NO: 2, the sequence of the nucleotide region at positions 1 to 615 in SEQ ID NO: 5, the sequence of the nucleotide region at positions 1 to 564 in SEQ ID NO: 8, the sequence of the nucleotide region at positions 1 to 528 in SEQ ID NO: 11, the sequence of the nucleotide region at positions 1 to 549 in SEQ ID NO: 14, or a sequence having an identity of at least 80% therewith and which contributes to formation of the three-dimensional structure of a mature protein region of the M23A subfamily protease located downstream thereof.

[4] The method according to [2], wherein the polynucleotide encoding a proprotein of the M23A family protease is preferably:

a polynucleotide which consists of a nucleotide sequence having an identity of at least 80% with the nucleotide sequence of SEQ ID NO: 2 and comprises a nucleotide sequence encoding the M23A family protease in a region corresponding to the nucleotide region at positions 523 to 1062 in SEQ ID NO: 2;

a polynucleotide which comprises the sequence of the nucleotide region at positions 1 to 522 in SEQ ID NO: 2 or a sequence having an identity of at least 80% therewith and encoding a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 3 and comprises a nucleotide sequence encoding the M23A family protease in a region corresponding to the nucleotide region at positions 595 to 1134 in SEQ ID NO: 3;

a polynucleotide which comprises the sequence of the nucleotide region at positions 1 to 594 in SEQ ID NO: 3 or a sequence having an identity of at least 80% therewith and encoding a secretion signal and a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 5 and comprises a nucleotide sequence encoding the M23A family protease in a region corresponding to the nucleotide region at positions 616 to 1164 in SEQ ID NO: 5;

a polynucleotide which comprises the sequence of the nucleotide region at positions 1 to 615 in SEQ ID NO: 5 or a sequence having an identity of at least 80% therewith and encoding a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 6 and comprises a nucleotide sequence encoding the M23A family protease in a region corresponding to the nucleotide region at positions 709 to 1257 in SEQ ID NO: 6;

a polynucleotide which comprises the sequence of the nucleotide region at positions 1 to 708 in SEQ ID NO: 6 or a sequence having an identity of at least 80% therewith and encoding a secretion signal and a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 8 and comprises a nucleotide sequence encoding the M23A family protease in a region corresponding to the nucleotide region at positions 565 to 1104 in SEQ ID NO: 8;

a polynucleotide which comprises the sequence of the nucleotide region at positions 1 to 564 in SEQ ID NO: 8 or a sequence having an identity of at least 80% therewith and encoding a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 9 and comprises a nucleotide sequence encoding the M23A family protease in a region corresponding to the nucleotide region at positions 625 to 1164 in SEQ ID NO: 9;

a polynucleotide which comprises the sequence of the nucleotide region at positions 1 to 624 in SEQ ID NO: 9 or a sequence having an identity of at least 80% therewith and encoding a secretion signal and a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 11 and comprises a nucleotide sequence encoding the M23A family protease in a region corresponding to the nucleotide region at positions 529 to 1065 in SEQ ID NO: 11;

a polynucleotide which comprises the sequence of the nucleotide region at positions 1 to 528 in SEQ ID NO: 11 or a sequence having an identity of at least 80% therewith and encoding a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 12 and comprises a nucleotide sequence encoding the M23A family protease in a region corresponding to the nucleotide region at positions 628 to 1164 in SEQ ID NO: 12;

a polynucleotide which comprises the sequence of the nucleotide region at positions 1 to 627 in SEQ ID NO: 12 or a sequence having an identity of at least 80% therewith and encoding a secretion signal and a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 14 and comprises a nucleotide sequence encoding the M23A family protease in a region corresponding to the nucleotide region at positions 550 to 1086 in SEQ ID NO: 14;

a polynucleotide which comprises the sequence of the nucleotide region at positions 1 to 549 in SEQ ID NO: 14 or a sequence having an identity of at least 80% therewith and encoding a proregion of the M23A subfamily protease and comprises a sequence encoding the M23A family protease linked downstream thereof;

a polynucleotide which consists of a nucleotide sequence having an identity of at least 80% with the nucleotide sequence of SEQ ID NO: 15 and comprises a nucleotide sequence encoding the M23A family protease in a region corresponding to the nucleotide region at positions 628 to 1164 in SEQ ID NO: 15; or a polynucleotide which comprises the sequence of the nucleotide region at positions 1 to 627 in SEQ ID NO: 15 or a sequence having an identity of at least 80% therewith and encoding a secretion signal and a proregion of the M23A subfamily protease and comprises a sequence encoding the M23A family protease linked downstream thereof.

[5] The method according to any one of [1] to [4], wherein the polynucleotide encoding a proprotein of the M23A family protease preferably further comprises a secretion signal region.

[6] The method according to [5], wherein the secretion signal region is preferably a secretion signal region derived from bacteria of the genus *Bacillus.*

[7] The method according to any one of [1] to [6], wherein the bacteria of the genus *Bacillus* are preferably bacteria which extracellularly secretes the protease or releases the protease with lysis of the bacteria.

[8] The method according to [7], wherein the bacteria of the genus *Bacillus* preferably have an extracellular protease activity.

[9] The method according to [7] or [8], wherein the proteases are preferably at least one selected from the group consisting of extracellular proteases encoded by aprE, epr, wprA, mpr, nprB, bpr, nprE, vpr, aprX, and a gene corresponding thereto.

[10] The method according to any one of [1] to [9], wherein the bacteria of the genus *Bacillus* are preferably *Bacillus subtilis* or a mutant strain thereof.

[11] The method according to any one of [1] to [10], preferably further comprising collecting the M23A family protease from the obtained culture broth.

EXAMPLES

Hereinafter, the present invention will be further specifically described with reference to examples.

However, the technical range of the present invention is not limited to these examples.

Table 2 shows the sequences of the primers used in the following examples.

TABLE 2

| Primer name | Sequence | SEQ ID NO. |
|---|---|---|
| BLP_S237signal_F | gaaggaaacactcgtatgaaaaaaatctcaaaagc | 21 |
| BLP_S237signal_R | aactagtttaatagattagttcggtccaggattcac | 22 |
| vector-F | tctattaaactagttatagggttatctaaagg | 23 |
| vector-sig-R | acgagtgtttccttctgctgc | 24 |
| ΔBLPsig_F | tgcagcatctgctcagggacatggattaa | 25 |
| ΔBLPsig_R | tgagcagatgctgcaagagctgccggaa | 26 |
| BLPsig_F | ttaggaggtaatatgatgaaaaaaatctcaaaagctggtctgg | 27 |
| BLPsig_R | catattacctcctaaatatttttaaagtaattgaatc | 28 |
| Δpro_F | ttgcagcatctccgaatggactgcttca | 29 |
| Δpro_R | tcggagatgctgcaagagctgccggaa | 30 |
| ΔBLPsig2_F | tctgctcagggacatggattaag | 31 |
| amyEsig(BLP)_F | ttaggaggtaatatgatgtttgcaaaacgattcaaaacctctttactg | 32 |
| amyEsig(BLP)_R | atgtccctgagcagaagcactcgcagccgccggt | 33 |
| BLP_FLAG_F | acaaagatgatgatgataaataatctattaaactagttatagggttatctaaagg | 34 |
| BLP_FLAG_R | catcatcatctttgtaatcgttcggtccaggattcac | 35 |
| LasA_F | gcagctcttgcagcacatgatgatggcctg | 36 |
| LasA_CR | tagtttaatagattagtggtggtggtggtgcagagccagtcccgg | 37 |
| pHY_just_F | taatctattaaactagttatagggttatctaaagg | 38 |
| pHY_just_R_NEW | tgctgcaagagctgccggaaa | 39 |
| LasA_Chis_n_R | cagagccagtcccggattatac | 40 |
| AhP_F | ttaggaggtaatatgatgtctcgtccgatcc | 41 |
| AhP_R | aactagtttaatagattagtcgattccgtt | 42 |
| vector-R | catattacctcctaaatatttttaaagtaattg | 43 |
| LgBLP_F | gcagctcttgcagcagcggaacgtggtctgagc | 44 |
| LgBLP_R | tagtttaatagattagtgacccggattggtgaacc | 45 |
| LaBLP_F | gcagctcttgcagcaggcggtcgtgatgcgaatg | 46 |
| LaBLP_R | tagtttaatagattacggattggtgaagtagccg | 47 |
| ΔS237N_fw | tgcagcaatgaaaaaaatctcaaaagctggtctgg | 48 |
| ΔS237N_rv | tttttcattgctgcaagagctgccggaa | 49 |
| 2R_*bacillus*-Chis | aactagtttaatagattagtggtggtggtggtggtcgattccgtt | 50 |

Example 1: BLP Production by Recombinant *Bacillus subtilis*

(1-1) Construction of BLP Expression Plasmid

Plasmid pUC57 with BLP gene (SEQ ID NO: 3) inserted therein (BLP/pUC57) was produced using an artificial gene synthesis service available from GenScript. PCR was performed using BLP/pUC57 as a template and a primer pair BLP_S237signal_F/BLP_S237signal_R (SEQ ID NOs: 21 and 22) and PrimeSTAR Max Premix (Takara Bio Inc). PCR was performed in the same manner using the plasmid pHY-S237 described in Example 7 of WO 2006/068148A1 as a template and a primer pair vector-F/vector-sig-R (SEQ ID NOs: 23 and 24). Each PCR product was treated with DpnI (New England Biolabs). Using the fragments obtained, In-Fusion reaction was performed according to the protocol of In-Fusion HD Cloning kit (Clontech). The In-Fusion reaction solution was transformed into ECOS™ Competent *E. coli* DH5α (310-06236, NIPPON GENE CO., LTD.) to construct a plasmid (pHY-BLP).

(A) pHY-BLP2

PCR was performed using pHY-BLP as a template and a primer pair ΔBLPsig_F/ΔBLPsig_R (SEQ ID NOs: 25 and 26). The PCR product was transformed into *E. coli* HST08 Premium Competent Cells (Takara Bio Inc.) to construct a plasmid (pHY-BLP2). The plasmid pHY-BLP2 consists of a BLP gene expression sequence with an S237 promoter sequence (SEQ ID NO: 16), an S237 secretion signal sequence (SEQ ID NO: 18), a sequence encoding the BLP proprotein (proregion+mature form), and an S237 terminator sequence linked in this order and a pHY300PLK vector sequence.

(B) pHY-BLP3

PCR was performed using pHY-BLP as a template and a primer pair BLPsig_F/BLPsig_R (SEQ ID NOs: 27 and 28). The PCR product was transformed into *E. coli* HST08 Premium Competent Cells (Takara Bio Inc.) to construct a plasmid (pHY-BLP3). The plasmid pHY-BLP3 consists of a BLP gene expression sequence with an S237 promoter sequence (SEQ ID NO: 16), a sequence encoding the BLP preproprotein (secretion signal+proregion+mature form), and an S237 terminator sequence linked in this order and a pHY300PLK vector sequence.

(C) pHY-BLP4

PCR was performed using pHY-BLP2 as a template and a primer pair Δpro_F/Δpro_R (SEQ ID NOs: 29 and 30). The PCR product was transformed into *E. coli* HST08 Premium Competent Cells (Takara Bio Inc.) to construct a plasmid (pHY-BLP4). The plasmid pHY-BLP4 consists of a BLP gene expression sequence with an S237 promoter sequence (SEQ ID NO: 16), an S237 secretion signal sequence (SEQ ID NO: 18), a sequence encoding a mature protein of BLP, and an S237 terminator sequence linked in this order and a pHY300PLK vector sequence.

(D) pHY-BLP5

PCR was performed using pHY-BLP as a template and a primer pair ΔBLPsig2_F/BLPsig_R (SEQ ID NOs: 31 and 28). PCR was performed in the same manner using *Bacillus subtilis* 168 strain (*Bacillus subtilis* Marburg No. 168 strain: Nature, 1997, 390, p. 249) genomic DNA as a template and a primer pair amyEsig(BLP)_F/amyEsig(BLP)_R (SEQ ID NOs: 32 and 33). Using the fragments obtained, In-Fusion reaction was performed to construct a plasmid (pHY-BLP5). The plasmid pHY-BLP5 consists of a BLP gene expression sequence with an S237 promoter sequence (SEQ ID NO: 16), an amyE secretion signal sequence (SEQ ID NO: 20), a sequence encoding the BLP proprotein (proregion+mature form), and an S237 terminator sequence linked in this order and a pHY300PLK vector sequence.

(1-2) Production of Recombinant *Bacillus subtilis*

*Bacillus subtilis* 168 strain was used as a host. The BLP expression plasmids pHY-BLP2 to 5 obtained in (1-1) and an empty vector pHY300PLK (Takara Bio Inc.) were each introduced into a host by the following method. The *Bacillus subtilis* 168 strain was inoculated into 1 mL of an LB culture medium and cultured with shaking at 30° C. and 200 spm overnight. 10 μL of the culture solution obtained was inoculated into 1 mL of a new LB culture medium and cultured at 37° C. and 200 spm for 3 hours. The culture solution was centrifuged to collect pellets. 500 μL of SMMP (0.5 M sucrose, 20 mM disodium maleate, 20 mM magnesium chloride hexahydrate, and 35% (w/v) Antibiotic medium 3 (Difco)) containing 4 mg/mL of lysozyme (SIGMA) was added to the pellets, and the mixture was incubated at 37° C. for 1 hour. Thereafter, the pellets were collected by centrifugation and suspended in 400 μL of SMMP. 33 μL of the suspension was mixed with 20 ng of each plasmid, further 100 μL of 40% (w/v) PEG was added thereto and stirred, further 350 μL of SMMP was added thereto, and thereafter the mixture was shaken at 30° C. for 1 hour. 200 μL of the solution obtained was smeared onto a DM3 regeneration agar medium (0.8% agar (Wako Pure Chemical Industries, Ltd.), 0.5% disodium succinate hexahydrate, 0.5% casamino acid technical (Difco), 0.5% yeast extract, 0.35% monopotassium phosphate, 0.15% dipotassium phosphate, 0.5% glucose, 0.4% magnesium chloride hexahydrate, 0.01% bovine serum albumin (SIGMA), 0.5% carboxymethylcellulose, 0.005% trypan blue (Merck KGaA) and an amino acid mixed solution (tryptophan, lysine, and methionine, 10 μg/mL each); where % represents (w/v) %) containing tetracycline (15 μg/mL, SIGMA) and was incubated at 30° C. for 3 days, to acquire colonies formed.

(1-3) Culture of Recombinant *Bacillus subtilis* and Acquisition of Culture Supernatant The recombinant *Bacillus subtilis* colonies obtained in (1-2) were inoculated into 1 mL of an LB culture medium with tetracycline added to a final concentration of 15 ppm, followed by culturing at 30° C. and 150 spm overnight. On the next day, 400 μL of the culture solution was inoculated into 5 mL of a 2×L-maltose medium (2% trypton, 1% yeast extract, 1% NaCl, 7.5% maltose, 7.5 ppm manganese sulfate pentahydrate, 21 μM $ZnSO_4$, and 15 ppm tetracycline; where % represents (w/v) %) and cultured at 30° C. and 150 spm for 2 days, and thereafter the culture supernatant was collected by centrifugation.

(1-4) Measurement of Enzymatic Activity in Culture Supernatant

A FRET substrate [which will be hereinafter referred to as FRET-GGGGG] (made to order by PH Japan Co., Ltd.) with pentaglycine located between a fluorescence group Nma and a quenching group Lys (Dpn) was used as a substrate. Here, Nma means 2-(N-methylamino)benzoyl (Nma). Further, Lys (Dpn) means those having 2,4-dinitrophenyl (Dnp) in the side chain of lysine (Lys). 2 μL of the culture supernatant (appropriately diluted) obtained in (1-3) and 200 μL of 20 mM Tris-HCl (pH7.5) were added to a 96-well assay plate (3881-096, AGC TECHNO GLASS CO., LTD.), and 10 μL of an FRET-GGGGG solution (1 mM FRET-GGGGG, 100 mM Tris-HCl (pH7.5)) was further added thereto to prepare a reaction solution. Using infinite M200 (TECAN), the fluorescence intensity of the reaction solution was measured over time at a temperature of 30° C., an excitation wavelength of 340 nm, and a measurement wavelength of 440 nm. Under the same reaction conditions, the fluorescence intensity was measured for a reaction solution prepared by using 20 mM Tris-HCl (pH7.5) instead of the enzyme solution and using an equimolar solution such as FRETS-25-STD1 and FRETS-25-STD2 (PEPTIDE INSTITUTE, INC.) instead of the FRET-GGGGG reaction solution to plot a calibration curve. The activity per unit (U) was defined as the amount of enzyme necessary for exhibiting a change in fluorescence intensity at X/min, supposing that the fluorescence intensity of a solution containing 1 μmol of FRETS-25-STD1 and 1 μmol of FRETS-25-STD2 is X. The FRET-GGGGG-degrading activity (U/mL) of the culture supernatant was determined.

FIG. 1 shows the measurement results. No FRET-GGGGG-degrading activity was detected in the culture supernatant of the recombinant strain with an empty vector introduced thereinto, but FRET-GGGGG-degrading activity was detected in the culture supernatant of the recombinant strain with plasmids (pHY-BLP2, 3, and 5) encoding the BLP proprotein introduced thereinto. It was demonstrated from this that an enzyme having an activity of degrading glycine-glycine bonds was present in the culture supernatant of the recombinant *Bacillus subtilis* with the polynucleotide encoding the BLP proprotein introduced. Further, the FRET-GGGGG-degrading activity was high in the culture supernatants of the recombinant strains with the plasmid (pHY-BLP2) containing the S237 secretion signal and the plasmid (pHY-BLP5) containing the amyE secretion signal introduced thereinto, as compared with the recombinant strain with the plasmid (pHY-BLP3) containing the original secretion signal of BLP introduced thereinto. It was demonstrated from this that the productivity of BLP was improved by linking a secretion signal which efficiently functions in *Bacillus subtilis* to the proprotein. Further, the fact that no FRET-GGGGG-degrading activity was detected in the culture supernatant of the recombinant strain having the plasmid (pHY-BLP4) free from the proregion of BLP introduced thereinto demonstrated that the proregion is essential for producing a BLP mature form.

(1-5) SDS-Page

Phenylmethylsulfonyl fluoride (NACALAI TESQUE, INC.) was mixed with the culture supernatant obtained in (1-3) to a final concentration of 2 mM. The mixed solution was mixed at 1:1 with a 2×Laemmli Sample Buffer (Bio-Rad) with 25 mM dithiothreitol (Thermo Fisher Scientific) added, followed by heating at 100° C. for 5 minutes. Using the solution obtained as a sample and Any kD™ Mini Protean TGX™ stain-free gel (Bio-Rad), SDS-PAGE was performed. As a marker, Precision Plus Protein™ uncolored standard (Bio-Rad) was used.

As a result of the SDS-PAGE, a band was detected at the position of the BLP mature form (19.3 kDa) in the culture supernatants of the recombinant *Bacillus subtilis* having the plasmids (pHY-BLP2 and 3) encoding the BLP proprotein introduced thereinto (FIG. 2).

Example 2: Influence of extracellular protease on mature BLP production (2-1) Construction of BLP-FLAG expression plasmid Using the plasmid pHY-BLP2 obtained in (1-1) as a template and a primer pair BLP_FLAG_F/BLP_FLAG R (SEQ ID NO: 34 and 35) and PrimeSTAR Max Premix (Takara Bio Inc.), PCR was performed. The PCR product was treated with DpnI (New England Biolabs), and the reaction solution was transformed into ECOS™ Competent *E. coli* DH5α (NIPPON GENE CO., LTD., 310-06236) to construct a plasmid (pHY-BLP-FLAG). The plasmid consists of a BLP-FLAG gene expression sequence with an 5237 promoter sequence (SEQ ID NO: 16), an S237 secretion signal sequence (SEQ ID NO: 18), a sequence encoding the BLP proprotein and having a FLAG (Trade Mark) tag (the amino acid sequence of DYKDDDDK) added at the C-terminus, and an S237 terminator sequence linked in this order and a pHY300PLK vector sequence.

(2-2) Production of Recombinant *Bacillus subtilis* and Acquisition of Culture Supernatant

*Bacillus subtilis* 168 strain and *Bacillus subtilis* Dpr9 strain (Kao9 strain produced in Examples 1 to 5 of JP-A-2006-174707) lacking 9 types of extracellular protease genes (aprE, epr, wprA, mpr, nprB, bpr, nprE, vpr and aprX) were used as hosts. The plasmid pHY-BLP-FLAG obtained in (2-1) and an empty vector pHY300PLK (Takara Bio Inc.) were each introduced into the hosts by the same procedure as in (1-2) to acquire colonies of the recombinant *Bacillus subtilis*. The recombinant *Bacillus subtilis* colonies obtained were cultured by the same procedure as in (1-3) to obtain culture supernatants.

(2-3) Measurement of Enzymatic Activity in Culture Supernatant and Western Blotting The enzymatic activity in each culture supernatant obtained in (2-2) was measured by the same procedure as in (1-4). Further, using the culture supernatant obtained in (2-2), SDS-PAGE was performed by the same procedure as in (1-5). The gel after the SDS-PAGE was transcribed into a PVDF membrane using a Trans-Blot Turbo™ system (Bio-Rad) and Trans-Blot Turbo™ Mini PVDF Transfer Packs (Bio-Rad). The membrane after the transcription was reacted with an HRP labeled anti-DYKDDDDK antibody (CST) using an iBind Western System (Life Technologies), and thereafter the target protein was detected using ImmunoStar™ Zeta (FUJIFILM Wako Pure Chemical Corporation).

As a result of the measurement of the enzymatic activity, the FRET-GGGGG-degrading activity was detected in the recombinant 168 strain, but no FRET-GGGGG-degrading activity was detected in the recombinant Dpr9 strain lacking extracellular protease (FIG. 3). As a result of the Western blotting, a band was detected at the position of the BLP mature form (19.3 kDa) in the recombinant 168 strain, but a band was detected at the position of the BLP proprotein (38.1 kDa) in the recombinant Dpr9 strain (FIG. 4). These results demonstrated that the extracellular protease in the culture broth plays an important role in producing an active BLP mature form, in particular, maturing BLP.

Meanwhile, the FRET-GGGGG-degrading activity was measured in the culture supernatants of all of the 9 protease-deficient strains (Δepr strain, ΔwprA strain, Δmpr strain, ΔnprB strain, Δbpr strain, ΔnprE strain, Δvpr strain, ΔaprE strain, and ΔaprX strain). 8 strains out of the above strains exhibited 80% or more activity with respect to the 168 strain. The remaining 1 strain also had 50% or more FRET-GGGGG-degrading activity with respect to the 168 strain. These results and the results for the Dpr9 strain suggests that the extracellular protease contributes to the production of the active BLP mature form.

Example 3: Production of Various M23A Subfamily Proteases Using Recombinant *Bacillus subtilis*-1

(3-1) Construction of LasA Expression Plasmid

Plasmid pUC57 with LasA gene (SEQ ID NO: 6) inserted therein (LasA/pUC57) was produced using an artificial gene synthesis service available from GenScript. Using LasA/pUC57 as a template and a primer pair LasA_F/LasA_CR (SEQ ID NOs: 36 and 37), PCR was performed according to the protocol of PrimeSTAR Max Premix (Takara Bio Inc). Using pHY-S237 (WO 2006/068148 A1) as a template and a primer pair pHY_just_F/pHY_just_R_NEW (SEQ ID NOs: 38 and 39), PCR was performed in the same manner. Each PCR product was treated with DpnI (New England Biolabs). Using the fragments obtained, In-Fusion reaction was performed according to the protocol of In-Fusion HD Cloning kit (Clontech). The reaction solution was transformed into *E. coli* HST08 Premium Competent Cells (Takara Bio Inc.) to construct a plasmid (pHY-LasA). Using pHY-LasA as a template, a primer pair pHY_just_F/LasA_Chis_n_R (SEQ ID NOs: 38 and 40), and KOD-Plus-Mutagenesis Kit (TOYOBO), PCR, DpnI digestion, and ligation were performed. The reaction solution was transformed into *E. coli* HST08 Premium Competent Cells (Takara Bio Inc.) to construct a plasmid (pHY-LasA2). The pHY-LasA2 consists of a LasA gene expression sequence with an S237 promoter sequence (SEQ ID NO: 16), an S237 secretion signal sequence (SEQ ID NO: 18), a sequence encoding the LasA proprotein (proregion+mature form), and an S237 terminator sequence linked in this order and a pHY300PLK vector sequence.

(3-2) Construction of AhP Expression Plasmid

Plasmid pUC57 with AhP gene (SEQ ID NO: 9) inserted therein (AhP/pUC57) was produced using an artificial gene synthesis service available from GenScript. Using AhP/pUC57 as a template and a primer pair AhP_F/AhP_R (SEQ ID NOs: 41 and 42), PCR was performed according to the protocol of PrimeSTAR Max Premix (Takara Bio Inc). Using pHY-S237 (WO 2006/068148 A1) as a template and a primer pair vector-F/vector-R (SEQ ID NOs: 23 and 43), PCR was performed in the same manner. Each PCR product was treated with DpnI (New England Biolabs). Using the fragments obtained, In-Fusion reaction was performed according to the protocol of In-Fusion HD Cloning kit (Clontech). The reaction solution was transformed into *E. coli* HST08 Premium Competent Cells (Takara Bio Inc.) to construct a plasmid (pHY-AhP). The pHY-AhP consists of an AhP gene expression sequence with an S237 promoter sequence (SEQ ID NO: 16), an AhP secretion signal sequence, a sequence encoding the AhP proprotein (proregion+mature form), and an S237 terminator sequence linked in this order and a pHY300PLK vector sequence.

(3-3) Construction of LgBLP Expression Plasmid

Plasmid pUC57 with the gene (LgBLP gene, SEQ ID NO: 11) of BLP homolog (WP_057941690.1, which will be hereinafter referred to as LgBLP) derived from *Lysobacter gummosus* inserted therein (LgBLP/pUC57) was produced using an artificial gene synthesis service available from GenScript. Using LgBLP/pUC57 as a template and a primer pair LgBLP_F/LgBLP_R (SEQ ID NOs: 44 and 45), PCR was performed according to the protocol of PrimeSTAR Max Premix (Takara Bio Inc). Using pHY-S237 (WO 2006/068148 A1) as a template and a primer pair pHY_just_F/pHY_just_R_NEW (SEQ ID NOs: 38 and 39), PCR was performed in the same manner. Each PCR product was treated with DpnI (New England Biolabs). Using the fragments obtained, In-Fusion reaction was performed according to the protocol of In-Fusion HD Cloning kit (Clontech). The reaction solution was transformed into *E. coli* HST08 Premium Competent Cells (Takara Bio Inc.) to construct a plasmid (pHY-LgBLP). The pHY-LgBLP consists of an LgBLP gene expression sequence with an S237 promoter sequence (SEQ ID NO: 16), an S237 secretion signal sequence (SEQ ID NO: 18), a sequence encoding LgBLP proprotein (proregion+mature form), and an S237 terminator sequence linked in this order and a pHY300PLK vector sequence.

(3-4) Construction of LaBLP Expression Plasmid

Plasmid pUC57 with the gene (LaBLP gene, SEQ ID NO: 14) of BLP homolog (WP_057970430.1, which will be hereinafter referred to as LaBLP) derived from *Lysobacter antibioticus* inserted therein (LaBLP/pUC57) was produced using an artificial gene synthesis service available from GenScript. Using LaBLP/pUC57 as a template and a primer pair LaBLP_F/LaBLP_R (SEQ ID NOs: 46 and 47), PCR was performed according to the protocol of PrimeSTAR Max Premix (Takara Bio Inc). Using pHY-S237 (WO 2006/068148 A1) as a template and a primer pair pHY_just_F/pHY_just_R_NEW (SEQ ID NOs: 38 and 39), PCR was performed in the same manner. Each PCR product was treated with DpnI (New England Biolabs). Using the fragments obtained, In-Fusion reaction was performed according to the protocol of In-Fusion HD Cloning kit (Clontech). The reaction solution was transformed into *E. coli* HST08 Premium Competent Cells (Takara Bio Inc.) to construct a plasmid (pHY-LaBLP). The pHY-LaBLP consists of LaBLP gene expression sequence with an S237 promoter sequence (SEQ ID NO: 16), an S237 secretion signal sequence (SEQ ID NO: 18), a sequence encoding LaBLP proprotein (proregion+mature form), and an S237 terminator sequence linked in this order and a pHY300PLK vector sequence.

(3-5) Production of Recombinant *Bacillus subtilis*

*Bacillus subtilis* 168 strain was used as a host. The plasmids obtained in (3-1) to (3-4) and an empty vector pHY300PLK (Takara Bio Inc.) were each introduced into the host by the same procedure as in (1-2) to acquire colonies of recombinant *Bacillus subtilis.*

(3-6) Culture of Recombinant *Bacillus subtilis* and Acquisition of Culture Supernatant The recombinant *Bacillus subtilis* colonies obtained in (3-5) were cultured by the same procedure as in (1-3) to obtain a culture supernatant.

(3-7) Measurement of Enzymatic Activity in Culture Supernatant

The enzymatic activity in the culture supernatant obtained in (3-6) was measured by the same procedure as (1-4). In the measurement of the LasA activity, culture supernatants of an empty vector-introduced strain and a LasA expression plasmid-introduced strain concentrated 20 times by Amicon Ultra 10K (Merck KGaA Millipore) were used. As a result of the measurement, for all of the M23A subfamily protease, a higher FRET-GGGGG-degrading activity was detected in the culture supernatant of the recombinant *Bacillus subtilis* having the polynucleotide encoding the proprotein of the M23A subfamily protease introduced thereinto than the culture supernatant of the empty vector-introduced *Bacillus subtilis* (FIG. 5).

Example 4: Production of Various M23A Subfamily Proteases Using Recombinant *Bacillus subtilis*-2

(4-1) Preparation of Culture Supernatant Containing BLP (4-1-1) Production of Expression Vector Plasmid pUC57 with BLP gene (SEQ ID NO: 3) inserted therein (BLP/pUC57) was produced using an artificial gene synthesis service available from GenScript. Using BLP/pUC57 as a template and a primer pair BLP_S237_signal_F/BLP_S237_signal_R (SEQ ID NOs: 21 and 22) and PrimeSTAR Max Premix (Takara Bio Inc.), PCR reaction was performed. Using the plasmid pHY-S237 described in Example 7 of WO 2006/068148 A1 as a template and a primer pair vector-F/vector-sig-R (SEQ ID NOs: 23 and 24), PCR reaction was performed in the same manner. Each PCR product was treated with DpnI (New England Biolabs). Subsequently, In-Fusion reaction was performed according to the protocol of In-Fusion HD Cloning kit (Clontech).

Using the In-Fusion reaction solution, ECOS™Competent *E. coli* DH5α (310-06236, NIPPON GENE CO., LTD.) was transformed. The transformed cells were smeared on an LB plate containing ampicillin and cultured at 37° C. overnight. The colonies formed on the plate were inoculated into an LB culture medium containing ampicillin and cultured overnight. Thereafter, bacteria were collected to extract plasmid (BLP/pHY) using High Pure Plasmid Isolation Kit (Roche). Using the BLP/pHY extracted as a template and a primer pair ΔS237N_fw/ΔS237N_rv(SEQ ID NO: 48 and 49), PCR reaction was performed. The PCR product was transformed into *E. coli* HST08 Premium Competent Cells (Takara Bio Inc). The transformed cells were smeared on an LB plate containing ampicillin and cultured at 37° C. overnight. The colonies formed on the plate were inoculated into an LB culture medium containing ampicillin and cultured overnight. Thereafter, bacteria were collected to extract a plasmid (BLP2/pHY) using High Pure Plasmid Isolation Kit (Roche).

(4-1-2) Production of Enzyme-Producing Transformed Strain

*Bacillus subtilis* 168 strain (*Bacillus subtilis* Marburg No. 168 strain: Nature, 390, 1997, p. 249) was inoculated into 1 mL of an LB culture medium and cultured with shaking at 30° C. and 200 rpm overnight. 10 μL of the culture solution was inoculated into 1 mL of a new LB culture medium and cultured at 37° C. and 200 rpm for 3 hours. The culture solution was centrifuged to collect pellets. 500 μL of SMMP [0.5M sucrose, 20 mM disodium maleate, 20 mM magnesium chloride hexahydrate, and 35% (w/v) Antibiotic Medium 3 (Difco)] containing 4 mg/mL of lysozyme (SIGMA) was added to the pellets and incubated at 37° C. for 1 hour. Thereafter, the pellets were collected by centrifugation and suspended in 400 μL of SMMP. 13 μL of the suspension, 2 μL of the plasmid BLP2/pHY solution (10 mM Tris-HCl pH8.5, 34.2 ng/μL) obtained in (4-1-1), and 20 μL of SMMP were mixed together, 100 μL of 40% PEG was further added thereto and stirred, and 350 μL of SMMP was further added thereto, followed by shaking at 30° C. for 1 hour. 200 μL of this solution was smeared onto a DM3 regeneration agar medium [0.8% agar (Wako Pure Chemical Industries, Ltd.), 0.5% disodium succinate hexahydrate, 0.5% casamino acid technical (Difco), 0.5% yeast extract, 0.35% monopotassium phosphate, 0.15% dipotassium phosphate, 0.5% glucose, 0.4% magnesium chloride hexahydrate, 0.01% bovine serum albumin (SIGMA), 0.5% carboxymethylcellulose, 0.005% trypan blue (Merck KGaA) and an amino acid mixture (tryptophan, lysine, and methionine, 10 μg/mL each); where % represents (w/v) %]containing tetracycline (15 μg/mL, SIGMA) and incubated at 30° C. for 3 days, to acquire colonies formed.

(4-1-3) Enzyme Production Using Transformed Strain

Tetracycline was added to an LB culture medium to a final concentration of 15 ppm. The colonies of the *Bacillus subtilis* transformants obtained in (4-1-2) were inoculated into 5 mL of the culture medium and then cultured at 30° C. and 250 rpm overnight. On the next day, 400 μL of the culture solution was inoculated into 20 mL of a 2×L-maltose medium (2% trypton, 1% yeast extract, 1% NaCl, 7.5% maltose, 7.5 ppm manganese sulfate pentahydrate, 15 ppm tetracycline, and 6 ppm zinc sulfate heptahydrate; where % represents (w/v) %) and cultured at 32° C. and 230 rpm for 2 days. Thereafter, the culture supernatant containing the enzyme produced from the bacteria was collected by centrifugation.

(4-2) Preparation of Culture Supernatant Containing LasA

Plasmid pUC57 with LasA gene (SEQ ID NO: 6) inserted therein (LasA/pUC57) was produced using an artificial gene synthesis service available from GenScript. Using LasA/pUC57 as a template and a primer pair LasA_F/LasA_CR (SEQ ID NOs: 36 and 37), PCR reaction was performed according to the protocol of PrimeSTAR Max Premix (Takara Bio Inc). Using the plasmid pHY-5237 described in Example 7 of WO 2006/068148 A1 as a template and a primer pair pHY_just_F/pHY_just_R_NEW (SEQ ID NOs: 38 and 39), PCR reaction was performed in the same manner. Each PCR product was treated with DpnI (New England Biolabs). Subsequently, In-Fusion reaction was performed according to the protocol of In-Fusion HD Cloning kit (Clontech) to obtain a plasmid (LasA/pHY) solution.

Using the plasmid (LasA/pHY) solution obtained, *Bacillus subtilis* prsA gene expression-enhanced strain (prsA-Kc strain produced in Example 1 of JP-A-2007-49986) was transformed by the same procedure as in (4-1-2), to acquire colonies of *Bacillus subtilis* transformants. Tetracycline was added to a 2×L liquid medium to a final concentration of 15 ppm. The colonies of the *Bacillus subtilis* transformants were inoculated into 5 mL of the culture medium and then cultured at 30° C. and 250 rpm overnight. Pellets were collected from the culture solution, to extract plasmid LasA/pHY from the pellets. Using the plasmid LasA/pHY extracted as a template, a primer pair pHY_just_F/LasA_Chis_n_R (SEQ ID NOs: 38 and 40), and KOD-Plus-Mutagenesis Kit (TOYOBO), PCR reaction, digestion of the plasmid with DpnI, and ligation were performed, to obtain a plasmid (LasA2/pHY).

Using the plasmid (LasA2/pHY) obtained, transformation was performed in the same manner as in (4-1-2). At this time, *Bacillus subtilis* prsA gene expression-enhanced strain (prsA-Kc strain produced in Example 1 of JP-A-2007-49986) was used as a host. Then, the transformed strain obtained were cultured by the same procedure as in (4-1-3), and the culture supernatant containing the enzyme produced from the bacteria was collected.

(4-3) Preparation of Culture Supernatant Containing AhP

Plasmid pUC57 with AhP gene (SEQ ID NO: 9) inserted therein (AhP/pUC57) was produced using an artificial gene synthesis service available from GenScript. Using AhP/pUC57 as a template and a primer pair AhP_F/2R_bacillus-Chis (SEQ ID NOs: 41 and 50), PCR reaction was performed according to the protocol of PrimeSTAR Max Premix (Takara Bio Inc). Using the plasmid pHY-S237 described in Example 7 of WO 2006/068148 A1 as a template and a primer pair vector-F/vector-R (SEQ ID NOs: 23 and 43), PCR reaction was performed in the same manner. Each PCR product was treated with DpnI (New England Biolabs). Subsequently, In-Fusion reaction was performed according to the protocol of In-Fusion HD Cloning kit (Clontech), to obtain a plasmid (AhP/pHY) solution.

Using the plasmid (AhP/pHY) obtained, transformation was performed in the same manner as in (4-1-2). At this time, *Bacillus subtilis* 168 strain was used as a host. Then, the transformed strain obtained were cultured by the same procedure as in (4-1-3), and the culture supernatant containing the enzyme produced from the bacteria was collected.

(4-4) Preparation of Protease from Culture Supernatant

The target protease was prepared from each culture supernatant obtained in (4-1) to (4-3). The culture supernatant was buffer exchanged with BufferA using Amicon Ultra with fraction molecular weight of 10K (Merck KGaA Millipore). An enzyme was prepared from the solution after the buffer exchange using AKTA explorer 10S (GE health care). First, the solution obtained by the buffer exchange was passed through column 1, and then the adsorbed components in column 1 were eluted using BufferB. From the eluted fractions, a fraction solution exhibiting FRET-GGGGG-degrading activity was collected. Subsequently, the fraction solution collected was subjected to Size Exclusion Chromatography using 20 mM Tris-HCl (pH 7.5) and column 2 equilibrated with a 200 mM NaCl solution, to collect a fraction solution exhibiting FRET-GGGGG-degrading activity. The fraction solution collected was buffer exchanged with a 20 mM Tris-HCl (pH 7.5) solution using Amicon Ultra with fraction molecular weight of 10K, to obtain an enzyme solution containing the target protease. BufferA, BufferB, column 1, and column 2 used for each culture supernatant were as shown in Table 3.

TABLE 3

| | BLP | LasA | AhP |
|---|---|---|---|
| Buffer A | 10 mM citric acid-Na pH 6 | 10 mM citric acid-Na pH 6 | 20 mM phosphate buffer pH 8<br>200 mM NaCl |
| Buffer B | 10 mM citric acid-Na pH 6<br>200 mM NaCl | 10 mM citric acid-Na pH 6<br>200 mM NaCl | 20 mM phosphate buffer pH 8<br>200 mM NaCl<br>300 mM Imidazole pH 8 |
| Column 1 | TOYOPEARL GigaCap CM-650M (TOSOH CORPORATION) | TOYOPEARL GigaCap CM-650M (TOSOH CORPORATION) | HisTALON(TM) Superflow Cartridge (TaKaRa) |
| Column 2 | HiLoad 16/600 Superdex 75 pg (GE Healthcare) | HiLoad 16/600 Superdex 75 pg (GE Healthcare) | TSKgel G4000SWXL (TOSOH CORPORATION) |

Example 5: Measurement of *Bacillus subtilis* Extracellular Protease Activity (5-1) Culture of *Bacillus subtilis* and Acquisition of Culture Supernatant

*Bacillus subtilis* 168 strain, 9 extracellular protease-deficient strains (Δepr strain, ΔwprA strain, Δmpr strain, ΔnprB strain, Δbpr strain, ΔnprE strain, Δvpr strain, ΔaprE strain, and ΔaprX strain), and Dpr9 strain were each inoculated into 1 mL of an LB culture medium and then cultured at 30° C. and 150 spm overnight. On the next day, 400 μL of each culture solution was inoculated into 5 mL of a 2×L-maltose medium (2% trypton, 1% yeast extract, 1% NaCl, 7.5% maltose, 7.5 ppm manganese sulfate pentahydrate, and 21 μM $ZnSO_4$; where % represents (w/v) %) and cultured at 30° C. and 150 spm for 2 days. Thereafter, the culture supernatant was collected by centrifugation.

(5-2) Measurement of Azocasein-Degrading Activity in Culture Supernatant

Azocasein (SIGMA) was used as a substrate for measuring the activity of each protease contained in the culture supernatant. 50 μL of the culture supernatant obtained in (5-1) was added to the substrate solution (1% (w/v) azocasein and 50 mM Tris-HCl (pH 7.5)) to react at 37° C. for 18 hours. 2 mL of a 5% trichloroacetic acid aqueous solution was added thereto to stop the reaction, followed by centrifugation at 15000 rpm and 4° C. for 5 minutes. The supernatant was appropriately diluted, and then the absorbance at 340 nm was measured using a cuvette with an optical path length of 1 cm. A mixture of the culture supernatant and the 5% trichloroacetic acid aqueous solution added in the reversed order was used as a control. The culture supernatants with a statistically significant increase (t test, $p<0.05$) in absorbance as compared with the control detected were determined to have azocasein-degrading activity. As a result of the measurement, the azocasein-degrading activity was detected in the culture supernatants of 168 strain and 9 extracellular protease-deficient strains (Δepr strain, ΔwprA strain, Δmpr strain, ΔnprB strain, Δbpr strain, ΔnprE strain, Δvpr strain, ΔaprE strain, and ΔaprX strain). Meanwhile, such activity was not detected in the culture supernatant of Dpr 9 strain (lower than the detection limit). These results were consistent with the active BLP productivity (Table 4).

TABLE 4

| Strain | Azocasein-degrading activity of culture supernatant | Active BLP productivity |
|---|---|---|
| 168 | + | + |
| Δepr | + | + |
| ΔwprA | + | + |
| Δmpr | + | + |
| ΔnprB | + | + |
| Δbpr | + | + |
| ΔnprE | + | + |
| Δvpr | + | + |
| ΔaprE | + | + |
| ΔaprX | + | + |
| Dpr9 | − | − |

Example 6: Comparison in BLP Productivity with Natural BLP-Producing Bacteria (6-1) Culture of BLP-Producing Bacteria and Acquisition of Culture Supernatant Until now, only a method of culturing natural BLP-producing bacteria isolated has been practically shown as a method for producing active BLP. In this example, BLP was produced by natural BLP-producing bacteria, to compare the productivity with that of the BLP-producing recombinant *Bacillus subtilis* of Example 1.

*Achromobacter lyticus* M497-1 strain as natural BLP-producing bacteria was inoculated into 1 mL of an LB culture medium and then cultured at 30° C. and 150 spm overnight. On the next day, 400 μL of the culture solution was inoculated into 5 mL of a 2×L-maltose medium (2% trypton, 1% yeast extract, 1% NaCl, 7.5% maltose, 7.5 ppm manganese sulfate pentahydrate, and 21 μM $ZnSO_4$; where % represents (w/v) %) and cultured at 30° C. and 150 spm for 2 days. Thereafter, the culture supernatant was collected by centrifugation.

(6-2) Measurement of Enzymatic Activity in Culture Supernatant

The enzymatic activity in the culture supernatant obtained in (6-1) was measured by the same procedure as in (1-4). As a result of the measurement, 14 U/mL of the FRET-GGGGG-degrading activity was detected in the culture supernatant of the *Achromobacter lyticus* M497-1 strain. This was a significantly small value as compared with the activity by the mature BLP expression recombinant *Bacillus subtilis* of Example 1 (43, 594, and 613 U/mL, respectively, as shown in FIG. 1). The strain which produces BLP most efficiently in the previous reports is *Lysobacter* sp. IB-9374 strain disclosed in Non Patent Literature 3. However, the productivity was reported to be 2.4 times that of the *Achromobacter lyticus* M497-1 strain and seem to be far from the BLP productivity of the recombinant *Bacillus subtilis* of Example 1. From the above, the present invention is a technique having a significant advantage over existing techniques in not only heterologous expression but also productivity.

Although embodiments of the present invention have been described above, it should be understood that they are not intended to limit the present invention to the specific embodiments described above. Various other changes and modifications within the scope of the invention will be apparent to those skilled in the art. The literatures and patent applications cited herein are incorporated by reference as if they are fully set forth herein.

What is claimed is:

1. A method for producing a mature form of a target M23A subfamily protease, comprising:

(a) culturing bacteria of the genus *Bacillus* in culture broth, wherein:

the bacteria of the genus *Bacillus* that are cultured are *Bacillus subtilis* or a mutant strain thereof;

(ii) the bacteria have a polynucleotide encoding a proprotein of the target M23A subfamily protease introduced thereinto, and (iii) the polynucleotide encoding the proprotein of the M23A subfamily protease of part (ii) further comprises a polynucleotide that encodes a secretion signal region derived from bacteria of the genus *Bacillus* operably linked to the proprotein;

(b) expressing the proprotein encoded by the polynucleotide during the culturing;

(c) secreting or releasing the expressed proprotein from the bacteria into the extracellular culture broth; and (d) converting the secreted or released proprotein to the mature form of the target M23A subfamily protease in the extracellular culture broth through the enzymatic action of extracellular proteases that were secreted from or released by the bacteria and that are other than the target M23A subfamily protease, thereby producing the mature form of the target M23A subfamily protease extracellularly.

2. The method of claim 1, wherein the mature form of the target M23A subfamily protease is:

a polypeptide consisting of the amino acid sequence of SEQ ID NO: 1, 4, 7, 10, or 13; or a polypeptide consisting of an amino acid sequence having a sequence identity of at least 80% with the amino acid sequence of any one of SEQ ID NOs: 1, 4, 7, 10, and 13 and having an activity of degrading glycine-glycine bonds in a peptide sequence.

3. The method of claim 1, wherein the polynucleotide encoding the proprotein of the target M23A subfamily protease is:

a polynucleotide consisting of the nucleotide sequence of any one of SEQ ID NOs: 2, 3, 5, 6, 8, 9, 11, 12, 14, and 15; or a polynucleotide comprising a polynucleotide encoding a proregion of the target M23A subfamily protease and a polynucleotide encoding the mature form of the target M23A subfamily protease linked downstream thereof.

4. The method of claim 1, wherein the polynucleotide encoding the proprotein of the target M23A subfamily protease is:

a polynucleotide that consists of a nucleotide sequence having a sequence identity of at least 80% with the nucleotide sequence of SEQ ID NO: 2 and that comprises a nucleotide sequence encoding the mature form of the target M23A subfamily protease in a region corresponding to the nucleotide region at positions 523 to 1062 in SEQ ID NO: 2;

a polynucleotide that comprises the sequence of the nucleotide region at positions 1 to 522 in SEQ ID NO: 2 or a sequence having a sequence identity of at least 80% therewith that encodes a proregion of the target M23A subfamily protease and that comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 3 and that comprises a nucleotide sequence encoding the mature form of the target M23A subfamily protease in a region corresponding to the nucleotide region at positions 595 to 1134 in SEQ ID NO: 3;

a polynucleotide that comprises the sequence of the nucleotide region at positions 1 to 594 in SEQ ID NO: 3 or a sequence having a sequence identity of at least 80% therewith that encodes a secretion signal and a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 5 and comprises a nucleotide sequence encoding the mature form of the target M23A subfamily protease in a region corresponding to the nucleotide region at positions 616 to 1164 in SEQ ID NO: 5;

a polynucleotide that comprises the sequence of the nucleotide region at positions 1 to 615 in SEQ ID NO: 5 or a sequence having a sequence identity of at least 80% therewith that encodes a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 6 and comprises a nucleotide sequence encoding the mature form of the target M23A subfamily protease in a region corresponding to the nucleotide region at positions 709 to 1257 in SEQ ID NO: 6;

a polynucleotide that comprises the sequence of the nucleotide region at positions 1 to 708 in SEQ ID NO: 6 or a sequence having a sequence identity of at least 80% therewith that encodes a secretion signal and a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 8 and comprises a nucleotide sequence encoding the mature form of the target M23A subfamily protease in a region corresponding to the nucleotide region at positions 565 to 1104 in SEQ ID NO: 8;

a polynucleotide that comprises the sequence of the nucleotide region at positions 1 to 564 of SEQ ID NO: 8 or a sequence having a sequence identity of at least 80% therewith that encodes a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 9 and comprises a nucleotide sequence encoding the mature form of the target M23A subfamily protease in a region corresponding to the nucleotide region at positions 625 to 1164 in SEQ ID NO: 9;

a polynucleotide that comprises the sequence of the nucleotide region at positions 1 to 624 in SEQ ID NO: 9 or a sequence having a sequence identity of at least 80% therewith that encodes a secretion signal and a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 11 and comprises a nucleotide sequence encoding the mature form of the target M23A subfamily protease in a region corresponding to the nucleotide region at positions 529 to 1065 in SEQ ID NO: 11;

a polynucleotide that comprises the sequence of the nucleotide region at positions 1 to 528 in SEQ ID NO: 11 or a sequence having a sequence identity of at least 80% therewith that encodes a proregion of the M23A subfamily protease and comprises a sequence encoding the mature form of the M23A subfamily protease linked downstream thereof;

a polynucleotide that consists of a nucleotide sequence having a sequence identity of at least 80% with the nucleotide sequence of SEQ ID NO: 12 and comprises a nucleotide sequence encoding the mature form of the target M23A subfamily protease in a region corresponding to the nucleotide region at positions 628 to 1164 in SEQ ID NO: 12;

a polynucleotide that comprises the sequence of the nucleotide region at positions 1 to 627 in SEQ ID NO: 12 or a sequence having a sequence identity of at least 80% therewith that encodes a secretion signal and a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 14 and comprises a nucleotide sequence encoding the mature form of the target M23A subfamily protease in a region corresponding to the nucleotide region at positions 550 to 1086 in SEQ ID NO: 14;

a polynucleotide that comprises the sequence of the nucleotide region at positions 1 to 549 in SEQ ID NO: 14 or a sequence having a sequence identity of at least 80% therewith that encodes a proregion of the target M23A subfamily protease and comprises a sequence encoding the mature form of the target M23A subfamily protease linked downstream thereof;

a polynucleotide that consists of a nucleotide sequence having a sequence identity of at least 80% with the nucleotide sequence of SEQ ID NO: 15 and comprises a nucleotide sequence encoding the mature form of the target M23A subfamily protease in a region corresponding to the nucleotide region at positions 628 to 1164 in SEQ ID NO: 15; or a polynucleotide that comprises the sequence of the nucleotide region at positions 1 to 627 in SEQ ID NO: 15 or a sequence having a sequence identity of at least 80% therewith that encodes a secretion signal and a proregion of the target M23A subfamily protease and comprises a sequence encoding the mature form of the target M23A subfamily protease linked downstream thereof.

5. The method of claim 1, wherein, in part (d), the extracellular protease that is other than the target M23A subfamily protease was secreted from the bacteria.

6. The method of claim 1, wherein, in part (d), the extracellular protease that is other than the target M23A subfamily protease was released from the bacteria by lysis of the bacteria.

7. The method of claim 5, wherein the protease that is other than the target M23A subfamily protease is an extracellular protease encoded by at least one gene selected from the group consisting of aprE, epr, wprA, mpr, nprB, bpr, nprE, vpr, aprX, and a gene corresponding thereto.

8. The method of claim 1, further comprising collecting the mature form of the target M23A subfamily protease from the obtained culture broth.

* * * * *

SEQUENCE LISTING

```
<160> NUMBER OF SEQ ID NOS: 50

<210> SEQ ID NO 1
<211> LENGTH: 179
<212> TYPE: PRT
<213> ORGANISM: Achromobacter lyticus
<220> FEATURE:
<223> OTHER INFORMATION: beta-lytic metallopeptidase (BLP) mature
      protein

<400> SEQUENCE: 1

Ser Pro Asn Gly Leu Leu Gln Phe Pro Phe Pro Arg Gly Ala Ser Trp
1               5                   10                  15

His Val Gly Gly Ala His Thr Asn Thr Gly Ser Gly Asn Tyr Pro Met
            20                  25                  30

Ser Ser Leu Asp Met Ser Arg Gly Gly Gly Trp Gly Ser Asn Gln Asn
        35                  40                  45

Gly Asn Trp Val Ser Ala Ser Ala Ala Gly Ser Phe Lys Arg His Ser
    50                  55                  60

Ser Cys Phe Ala Glu Ile Val His Thr Gly Gly Trp Ser Thr Thr Tyr
65                  70                  75                  80

Tyr His Leu Met Asn Ile Gln Tyr Asn Thr Gly Ala Asn Val Ser Met
                85                  90                  95

Asn Thr Ala Ile Ala Asn Pro Ala Asn Thr Gln Ala Gln Ala Leu Cys
            100                 105                 110

Asn Gly Gly Gln Ser Thr Gly Pro His Glu His Trp Ser Leu Lys Gln
        115                 120                 125

Asn Gly Ser Phe Tyr His Leu Asn Gly Thr Tyr Leu Ser Gly Tyr Arg
    130                 135                 140

Ile Thr Ala Thr Gly Ser Ser Tyr Asp Thr Asn Cys Ser Arg Phe Tyr
145                 150                 155                 160

Leu Thr Lys Asn Gly Gln Asn Tyr Cys Tyr Gly Tyr Tyr Val Asn Pro
                165                 170                 175

Gly Pro Asn


<210> SEQ ID NO 2
<211> LENGTH: 1062
<212> TYPE: DNA
<213> ORGANISM: Achromobacter lyticus

<400> SEQUENCE: 2

tctgctcagg gacatggatt aagcggcgaa gatctggttt actcttacga tgaaatgttt      60

gattttgata tcgatgccta cctggcaaaa catgcgccgc atctgcataa acatagcgaa     120

gaaatctctc attgggccgg atattctggc atttcaccga aagttcttat cgcattaatg     180

gaacaacagt caggagctgt gagcgccaaa agagcaacaa atcgcccgtt tggcaaactt     240

gccagagcag atggatttgg cgcccaaaca cgcgaagtgg cgttagctct gagagaatct     300

ctttatgaac gcgatccgga tggagccaaa ggcccggtca cattagccag agcaaacccg     360

ctgcaggcac tttttgaacg ctcaggagat aatgaaccgg cagcggcttt aagaggagat     420

ggcgaatttc aacttgtcta cggcagatta tttaacgaac cgcgccaggc aaaagccgca     480

agcgatagat ttgcgaaagc tggaccggat gttcaaccgt tatctccgaa tggactgctt     540
```

```
cagtttccgt ttccgagagg cgcatcttgg catgtgggcg gagctcatac aaacacagga    600

tcaggcaatt atccgatgtc aagcctggat atgtcaagag gcggaggctg gggaagcaat    660

caaaacggca attgggtttc agcgagcgcg gctggatctt ttaaacgcca ttcttcatgc    720

tttgctgaaa ttgttcatac aggcggctgg tcaacaacat actaccatct gatgaacatc    780

cagtacaata caggcgcgaa cgttagcatg aatacagcca tcgcaaaccc ggctaataca    840

caagcgcagg ctctgtgcaa cggaggccaa agcacaggac cgcatgaaca ttggtcactg    900

aaacagaacg gctcatttta ccatctgaac ggaacatacc tttcaggcta tagaatcaca    960

gcgacaggca gctcttatga tacaaattgt agccgctttt atttgacaaa aaatggacag   1020

aactactgct atggttatta tgtgaatcct ggaccgaact aa                      1062
```

<210> SEQ ID NO 3
<211> LENGTH: 1134
<212> TYPE: DNA
<213> ORGANISM: Achromobacter lyticus

<400> SEQUENCE: 3

```
atgaaaaaaa tctcaaaagc tggtctggga ctggctctgg tctgtgctct ggcgacgatt     60

ggaggcaacg catctgctca gggacatgga ttaagcggcg aagatctggt ttactcttac    120

gatgaaatgt ttgattttga tatcgatgcc tacctggcaa aacatgcgcc gcatctgcat    180

aaacatagcg aagaaatctc tcattgggcc ggatattctg gcatttcacc gaaagttctt    240

atcgcattaa tggaacaaca gtcaggagct gtgagcgcca aaagagcaac aaatcgcccg    300

tttggcaaac ttgccagagc agatggattt ggcgcccaaa cacgcgaagt ggcgttagct    360

ctgagagaat ctctttatga acgcgatccg gatggagcca aaggcccggt cacattagcc    420

agagcaaacc cgctgcaggc actttttgaa cgctcaggag ataatgaacc ggcagcggct    480

ttaagaggag atggcgaatt tcaacttgtc tacggcagat tatttaacga accgcgccag    540

gcaaaagccg caagcgatag atttgcgaaa gctggaccgg atgttcaacc gttatctccg    600

aatggactgc ttcagtttcc gtttccgaga ggcgcatctt ggcatgtggg cggagctcat    660

acaaacacag gatcaggcaa ttatccgatg tcaagcctgg atatgtcaag aggcggaggc    720

tggggaagca atcaaaacgg caattgggtt tcagcgagcg cggctggatc ttttaaacgc    780

cattcttcat gctttgctga aattgttcat acaggcggct ggtcaacaac atactaccat    840

ctgatgaaca tccagtacaa tacaggcgcg aacgttagca tgaatacagc catcgcaaac    900

ccggctaata cacaagcgca ggctctgtgc aacggaggcc aaagcacagg accgcatgaa    960

cattggtcac tgaaacagaa cggctcattt taccatctga acggaacata cctttcaggc   1020

tatagaatca cagcgacagg cagctcttat gatacaaatt gtagccgctt ttatttgaca   1080

aaaaatggac agaactactg ctatggttat tatgtgaatc ctggaccgaa ctaa         1134
```

<210> SEQ ID NO 4
<211> LENGTH: 182
<212> TYPE: PRT
<213> ORGANISM: Pseudomonas aeruginosa
<220> FEATURE:
<223> OTHER INFORMATION: Las A protein (LAS) mature protein

<400> SEQUENCE: 4

```
Ala Pro Pro Ser Asn Leu Met Gln Leu Pro Trp Arg Gln Gly Tyr Ser
1               5                   10                  15

Trp Gln Pro Asn Gly Ala His Ser Asn Thr Gly Ser Gly Tyr Pro Tyr
```

-continued

```
            20                  25                  30

Ser Ser Phe Asp Ala Ser Tyr Asp Trp Pro Arg Trp Gly Ser Ala Thr
        35                  40                  45

Tyr Ser Val Val Ala Ala His Ala Gly Thr Val Arg Val Leu Ser Arg
    50                  55                  60

Cys Gln Val Arg Val Thr His Pro Ser Gly Trp Ala Thr Asn Tyr Tyr
65                  70                  75                  80

His Met Asp Gln Ile Gln Val Ser Asn Gly Gln Gln Val Ser Ala Asp
                85                  90                  95

Thr Lys Leu Gly Val Tyr Ala Gly Asn Ile Asn Thr Ala Leu Cys Glu
            100                 105                 110

Gly Gly Ser Ser Thr Gly Pro His Leu His Phe Ser Leu Leu Tyr Asn
        115                 120                 125

Gly Ala Phe Val Ser Leu Gln Gly Ala Ser Phe Gly Pro Tyr Arg Ile
    130                 135                 140

Asn Val Gly Thr Ser Asn Tyr Asp Asn Asp Cys Arg Arg Tyr Tyr Phe
145                 150                 155                 160

Tyr Asn Gln Ser Ala Gly Thr Thr His Cys Ala Phe Arg Pro Leu Tyr
                165                 170                 175

Asn Pro Gly Leu Ala Leu
            180
```

<210> SEQ ID NO 5
<211> LENGTH: 1164
<212> TYPE: DNA
<213> ORGANISM: Pseudomonas aeruginosa

<400> SEQUENCE: 5

```
catgatgatg gcctgccggc atttcgttat tcagccgaac tgctgggtca actgcagctg      60

ccgtctgtgg cactgccgct gaatgatgac ctgtttctgt atggccgtga tgcggaagca     120

tttgatctgg aagcgtatct ggcactgaat gcaccggcac tgcgtgataa aagcgaatat     180

ctggaacatt ggtcaggcta ttattctatt aatccgaaag ttctgctgac actgatggtc     240

atgcaaagcg gtccgctggg tgcaccggat gaacgtgcac tggcagcacc gctgggccgt     300

ctgtcagcca aacgcggttt tgatgcgcag gtgcgcgatg ttctgcagca gctgtctcgc     360

cgttattatg gctttgaaga atatcaactg cgccaggcag cagcacgtaa agcagttggc     420

gaagatggtc tgaatgcagc atctgcagcg ctgctgggcc tgctgcgtga aggtgcaaaa     480

gtcagcgcag tgcagggcgg taatccgctg ggtgcatatg cccagacctt tcagcgcctg     540

tttggtacac cggcggcaga actgctgcag ccgtcaaatc gtgttgcacg tcaactgcag     600

gcaaaagcgg cactggcacc gccgagcaac ctgatgcagc tgccgtggcg tcagggctat     660

tcatggcagc cgaatggtgc acatagcaac acgggctcag gttatccgta tagctcattt     720

gatgccagct atgattggcc gcgttggggc tctgcaacct atagcgtggt tgcagcccat     780

gcgggtacag tccgcgtgct gtctcgttgc caagttcgtg tcacacatcc gtctggttgg     840

gcaaccaatt attatcatat ggatcagatt caggtgagca acggtcagca ggtttcagca     900

gatacgaaac tgggcgttta tgcaggtaat atcaacacag ccctgtgcga aggcggttct     960

agcacgggcc cgcatctgca tttttctctg ctgtataatg gtgcgtttgt ctcactgcag    1020

ggcgcatctt ttggtccgta tcgcatcaac gtgggcacca gcaattatga taacgattgt    1080

cgccgttatt acttctacaa tcagtctgct ggaacaaccc actgtgcctt tagaccgctg    1140

tataatccgg gactggctct gtaa                                           1164
```

<210> SEQ ID NO 6
<211> LENGTH: 1257
<212> TYPE: DNA
<213> ORGANISM: Pseudomonas aeruginosa

<400> SEQUENCE: 6

```
atgcaacata aaagaagccg tgcgatggcg agcccgagaa gcccgttcct gtttgtgctg      60

ctggccctgg cggtgggtgg tactgccaac gcgcatgatg atggcctgcc ggcatttcgt     120

tattcagccg aactgctggg tcaactgcag ctgccgtctg tggcactgcc gctgaatgat     180

gacctgtttc tgtatggccg tgatgcggaa gcatttgatc tggaagcgta tctggcactg     240

aatgcaccgg cactgcgtga taaaagcgaa tatctggaac attggtcagg ctattattct     300

attaatccga aagttctgct gacactgatg gtcatgcaaa gcggtccgct gggtgcaccg     360

gatgaacgtg cactggcagc accgctgggc cgtctgtcag ccaaacgcgg ttttgatgcg     420

caggtgcgcg atgttctgca gcagctgtct cgccgttatt atggctttga agaatatcaa     480

ctgcgccagg cagcagcacg taaagcagtt ggcgaagatg gtctgaatgc agcatctgca     540

gcgctgctgg gcctgctgcg tgaaggtgca aaagtcagcg cagtgcaggg cggtaatccg     600

ctgggtgcat atgcccagac ctttcagcgc ctgtttggta caccggcggc agaactgctg     660

cagccgtcaa atcgtgttgc acgtcaactg caggcaaaag cggcactggc accgccgagc     720

aacctgatgc agctgccgtg gcgtcagggc tattcatggc agccgaatgg tgcacatagc     780

aacacgggct caggttatcc gtatagctca tttgatgcca gctatgattg gccgcgttgg     840

ggctctgcaa cctatagcgt ggttgcagcc catgcgggta cagtccgcgt gctgtctcgt     900

tgccaagttc gtgtcacaca tccgtctggt tgggcaacca attattatca tatggatcag     960

attcaggtga gcaacggtca gcaggtttca gcagatacga aactgggcgt ttatgcaggt    1020

aatatcaaca cagccctgtg cgaaggcggt tctagcacgg gcccgcatct gcatttttct    1080

ctgctgtata atggtgcgtt tgtctcactg cagggcgcat cttttggtcc gtatcgcatc    1140

aacgtgggca ccagcaatta tgataacgat tgtcgccgtt attacttcta caatcagtct    1200

gctggaacaa cccactgtgc ctttagaccg ctgtataatc cgggactggc tctgtaa       1257
```

<210> SEQ ID NO 7
<211> LENGTH: 179
<212> TYPE: PRT
<213> ORGANISM: Aeromonas hydrophila
<220> FEATURE:
<223> OTHER INFORMATION: Aeromonas hydrophila proteinase (AhP) mature protein

<400> SEQUENCE: 7

```
Ala Gly Gly Gln Phe Gln Leu Pro Trp Arg Gln Gly Tyr Ser Trp Lys
1               5                   10                  15

Ala Asn Gly Ala His Ser His Thr Gly Ser Gly Tyr Pro Tyr Ser Ser
            20                  25                  30

Ile Asp Val Ser Tyr Asp Trp Pro Gly Trp Gly Gly Ala Thr Tyr Thr
        35                  40                  45

Val Thr Ala Ala Asn Ser Gly Thr Val Thr Val Phe Ser Arg Cys Gln
    50                  55                  60

Val Arg Val Thr Ala Thr Asn Gly Trp Ala Thr Asn Tyr Tyr His Met
65                  70                  75                  80

Ser Gly Ile Ser Val Arg Ser Gly Asp Tyr Val Ala Ala Asp Thr Pro
                85                  90                  95
```

-continued

```
Ile Gly Thr Tyr Ala Ser Asn Arg Asn Glu Ala Leu Cys Glu Gly Gly
            100                 105                 110

Ser Ser Thr Gly Pro His Leu His Phe Ser Leu Leu Tyr Asn Gly Val
        115                 120                 125

Phe Gln Ser Leu Gln Gly Gln Arg Leu Ser Ser Tyr Ala Val Asn Val
    130                 135                 140

Gly Ala Ser Asn Tyr Asp Asp Asn Cys Asn Arg Phe Trp Leu Tyr Asn
145                 150                 155                 160

Gln Arg Asn Gly Gln Arg Tyr Cys Ala Trp Gln Pro Leu Tyr Asn Asn
                165                 170                 175

Gly Ile Asp
```

<210> SEQ ID NO 8
<211> LENGTH: 1104
<212> TYPE: DNA
<213> ORGANISM: Aeromonas hydrophila

<400> SEQUENCE: 8

```
ggcgatattc acgctccgct ggctccgtat cattttacgg cgcagcaact ggcagcatct     60

caaaccccgg cactgccgct ggatgaagca cattttgttt ttggcgaagc cgcgatggca    120

tttgatctgc atgattttct gctgcagcag gccccgcatc tgctgccgaa agaagaagtc    180

attctgcatt ggagcggtat cacgtcactg aatccgcagc tgctgctggc cctgatggaa    240

gcgagctcac agctgatttc agcaccgtct gaacaggcca tggcagcccc gtttgcgaaa    300

ctggtgaatg cacgtggctt tgataaccag ctggaactga tggcccgcca gctgtctgaa    360

cgtttttatc aggcacgcgc ccagcagaaa ctgatgcaac gttctgcacc ggcactggcc    420

ccgcaggcgg cacatcaggc cgcgctggca tcaatgctgt ctaccagcat gcagcgtcag    480

ctgggcgaac agtggcagac cctgtttggt caagatgcaa tgacaagccc gcgcggcggt    540

gcagcagcac cggcagcccc gctggcaggc ggtcaatttc agctgccgtg gcgtcagggc    600

tattcttgga aagcgaatgg tgcacattct catacaggca gcggttatcc gtattctagc    660

atcgatgtca gctatgattg gccgggttgg ggcggtgcga cctatacagt gacggcggca    720

aactcaggta ccgtgacagt gtttagccgt tgccaggtcc gtgtgacagc aaccaatggc    780

tgggcgacaa actattatca tatgagcggc atttcagtgc gttctggtga ttatgttgcc    840

gcggatacac cgatcggcac gtatgcctca aatcgcaacg aagcgctgtg cgaaggcggt    900

tcatctacgg gtccgcatct gcattttagc ctgctgtata atggcgtttt tcagtcactg    960

cagggtcagc gtctgagctc atatgcagtt aatgtcggcg ccagcaacta tgatgataat   1020

tgtaaccgct tttggctgta taaccaaaga aacggacaac gctactgtgc ttggcaaccg   1080

ctgtataata acggaatcga ctaa                                          1104
```

<210> SEQ ID NO 9
<211> LENGTH: 1164
<212> TYPE: DNA
<213> ORGANISM: Aeromonas hydrophila

<400> SEQUENCE: 9

```
atgtctcgtc cgatcccgtc cctgctgatg ctggctctgc tgccggctgc tggttgggct     60

ggcgatattc acgctccgct ggctccgtat cattttacgg cgcagcaact ggcagcatct    120

caaaccccgg cactgccgct ggatgaagca cattttgttt ttggcgaagc cgcgatggca    180

tttgatctgc atgattttct gctgcagcag gccccgcatc tgctgccgaa agaagaagtc    240
```

-continued

```
attctgcatt ggagcggtat cacgtcactg aatccgcagc tgctgctggc cctgatggaa    300

gcgagctcac agctgatttc agcaccgtct gaacaggcca tggcagcccc gtttgcgaaa    360

ctggtgaatg cacgtggctt tgataaccag ctggaactga tggcccgcca gctgtctgaa    420

cgtttttatc aggcacgcgc ccagcagaaa ctgatgcaac gttctgcacc ggcactggcc    480

ccgcaggcgg cacatcaggc cgcgctggca tcaatgctgt ctaccagcat gcagcgtcag    540

ctgggcgaac agtggcagac cctgtttggt caagatgcaa tgacaagccc gcgcggcggt    600

gcagcagcac cggcagcccc gctggcaggc ggtcaatttc agctgccgtg gcgtcagggc    660

tattcttgga aagcgaatgg tgcacattct catacaggca gcggttatcc gtattctagc    720

atcgatgtca gctatgattg gccgggttgg ggcggtgcga cctatacagt gacggcggca    780

aactcaggta ccgtgacagt gtttagccgt tgccaggtcc gtgtgacagc aaccaatggc    840

tgggcgacaa actattatca tatgagcggc atttcagtgc gttctggtga ttatgttgcc    900

gcggatacac cgatcggcac gtatgcctca aatcgcaacg aagcgctgtg cgaaggcggt    960

tcatctacgg gtccgcatct gcattttagc ctgctgtata atggcgtttt tcagtcactg   1020

cagggtcagc gtctgagctc atatgcagtt aatgtcggcg ccagcaacta tgatgataat   1080

tgtaaccgct tttggctgta taaccaaaga aacggacaac gctactgtgc ttggcaaccg   1140

ctgtataata acggaatcga ctaa                                          1164


<210> SEQ ID NO 10
<211> LENGTH: 178
<212> TYPE: PRT
<213> ORGANISM: Lysobacter gummosus
<220> FEATURE:
<223> OTHER INFORMATION: LgBLP mature protein

<400> SEQUENCE: 10

Ser Pro Asn Gly Leu Leu Gln Phe Pro Phe Pro Arg Gly Ala Arg Trp
1               5                   10                  15

His Val Gly Gly Ala His Thr Asn Thr Gly Ser Gly Asn Tyr Pro Met
            20                  25                  30

Ser Ser Leu Asp Met Ser Leu Gly Gly Gly Trp Gly Ser Asn Gln Ser
        35                  40                  45

Asn Thr Trp Val Ser Ala Ser Ala Asn Gly Ser Phe Lys Arg His Ser
    50                  55                  60

Ser Cys Phe Ala Glu Ile Val His Ser Gly Gly Trp Ser Thr Thr Tyr
65                  70                  75                  80

Tyr His Leu Met Asn Ile Arg Tyr Asn Thr Gly Ala Asn Val Gly Ser
                85                  90                  95

Asn Thr Ala Ile Ala Asn Pro Ala Asn Thr Arg Ala Gln Ala Leu Cys
            100                 105                 110

Asn Gly Gly Ser Ser Thr Gly Pro His Glu His Trp Ser Leu Lys Leu
        115                 120                 125

Asn Gly Ser Phe Tyr His Leu Asn Gly Ala Tyr Leu Ser Gly Tyr Arg
    130                 135                 140

Ile Thr Ala Thr Gly Ser Ser Tyr Asp Thr Asn Cys Ser Arg Phe Tyr
145                 150                 155                 160

Leu Ala Lys Asn Gly Gln Asn Tyr Cys Ser Gly Trp Phe Thr Asn Pro
                165                 170                 175

Gly His
```

<210> SEQ ID NO 11
<211> LENGTH: 1065
<212> TYPE: DNA
<213> ORGANISM: Lysobacter gummosus

<400> SEQUENCE: 11

```
gcggaacgtg gtctgagcgg ccaggacctg gtttatagct acgatgaaat gtttgatttc      60
gacattgatg cgtacctggc gaaaaacgcg ccgcatctga gccgtcacgc ggaaagcatc     120
agccattggg cgggttatag cggcattagc ccgaaagtgc tgatcgcgct gatggaacag     180
caaagcggcg cgattacccg taaacatgca gcagcagatg cagcaaaacg tccgtttggt     240
gcactggcga aagcgaaaga tttcaatggt cagacccgtg aagttgcgca agcgctgcgt     300
gaagcgctgt acgaaaacga cggtccggat gcaaagggtg cagttaccgt ggcacgtgca     360
aatccgctgc aggcactgtt tgaacgtgcg ggtgcaagcc aagcaagcgc aaaactgagc     420
ggtgacggcg aatttcagct ggtgtatggt cgtctgttca acgaaccgcg tcaggcacag     480
gcaccgagcg cacgttttgc aaaagcgggt ccggatgttc agccgctgag cccgaatggc     540
ctgctgcaat ttccgtttcc gcgtggtgcg cgttggcatg tgggcggtgc gcacaccaac     600
accggtagcg gcaattaccc gatgagcagc ctggacatga gcctgggcgg tggctggggc     660
agcaaccaaa gcaatacctg ggttagcgcg agcgcgaacg gtagctttaa acgtcatagc     720
agctgcttcg cggaaattgt gcacagcggt ggctggagca ccacctatta ccatctgatg     780
aacattcgtt acaataccgg tgcgaacgtt ggcagcaata ccgcgattgc aaatccggca     840
aatacccgtg cacaggcact gtgcaatggt ggcagcagca ccggcccgca tgaacactgg     900
agcctgaaac tgaacggtag cttttatcat ctgaatggtg cgtatctgag cggctaccgt     960
atcaccgcga ccggcagcag ctatgatacc aactgcagcc gtttttacct ggcgaaaaac    1020
ggtcaaaatt attgcagcgg ctggttcacc aatccgggtc actaa                    1065
```

<210> SEQ ID NO 12
<211> LENGTH: 1164
<212> TYPE: DNA
<213> ORGANISM: Lysobacter gummosus

<400> SEQUENCE: 12

```
atgtctaaca aaacaggatc taaccaggca ttttctaaaa tgggattagc attattaaca      60
tgctgcgttt tagcagcaat ctctggagga gcaggagcag cggaacgtgg tctgagcggc     120
caggacctgg tttatagcta cgatgaaatg tttgatttcg acattgatgc gtacctggcg     180
aaaaacgcgc cgcatctgag ccgtcacgcg gaaagcatca gccattgggc gggttatagc     240
ggcattagcc cgaaagtgct gatcgcgctg atggaacagc aaagcggcgc gattacccgt     300
aaacatgcag cagcagatgc agcaaaacgt ccgtttggtg cactggcgaa agcgaaagat     360
ttcaatggtc agacccgtga agttgcgcaa gcgctgcgtg aagcgctgta cgaaaacgac     420
ggtccggatg caaagggtgc agttaccgtg gcacgtgcaa atccgctgca ggcactgttt     480
gaacgtgcgg gtgcaagcca agcaagcgca aaactgagcg gtgacggcga atttcagctg     540
gtgtatggtc gtctgttcaa cgaaccgcgt caggcacagg caccgagcgc acgttttgca     600
aaagcgggtc cggatgttca gccgctgagc ccgaatggcc tgctgcaatt tccgtttccg     660
cgtggtgcgc gttggcatgt gggcggtgcg cacaccaaca ccggtagcgg caattacccg     720
atgagcagcc tggacatgag cctgggcggt ggctggggca gcaaccaaag caatacctgg     780
gttagcgcga gcgcgaacgg tagctttaaa cgtcatagca gctgcttcgc ggaaattgtg     840
```

```
cacagcggtg gctggagcac cacctattac catctgatga acattcgtta caataccggt    900

gcgaacgttg gcagcaatac cgcgattgca aatccggcaa atacccgtgc acaggcactg    960

tgcaatggtg gcagcagcac cggcccgcat gaacactgga gcctgaaact gaacggtagc   1020

ttttatcatc tgaatggtgc gtatctgagc ggctaccgta tcaccgcgac cggcagcagc   1080

tatgatacca actgcagccg tttttacctg gcgaaaaacg gtcaaaatta ttgcagcggc   1140

tggttcacca atccgggtca ctaa                                          1164
```

```
<210> SEQ ID NO 13
<211> LENGTH: 178
<212> TYPE: PRT
<213> ORGANISM: Lysobacter antibioticus
<220> FEATURE:
<223> OTHER INFORMATION: LaBLP mature protein

<400> SEQUENCE: 13

Ala Gly Pro Ala Asn Gly Phe Leu Gln Phe Pro Tyr Pro Arg Gly Ala
1               5                   10                  15

Ser Trp His Val Gly Gly Ala His Thr Asn Thr Gly Ser Gly Asn Tyr
            20                  25                  30

Pro Met Ser Ser Leu Asp Met Ser Arg Gly Gly Gly Trp Gly Ser Asn
        35                  40                  45

Gln Ser Gly Asn Trp Val Ser Ala Ser Ala Gly Gly Ser Phe Lys Arg
    50                  55                  60

His Ser Ser Cys Phe Ala Glu Val Val His Ser Gly Gly Trp Ser Thr
65                  70                  75                  80

Thr Tyr Tyr His Met Met Asn Leu Gln Tyr Gly Thr Gly Ala Ser Val
                85                  90                  95

Ala Ala Asn Ser Arg Ile Gly Asn Pro Ala Asn Thr Arg Ala Gln Ala
            100                 105                 110

Leu Cys Asn Gly Gly Ala Ser Thr Gly Pro His Glu His Trp Ser Leu
        115                 120                 125

Lys Tyr Asn Gly Ser His Tyr His Leu Asn Gly Val Tyr Leu Ser Gly
    130                 135                 140

Tyr Gln Ile Thr Ala Leu Gly Ser Ser Tyr Asp Thr Asn Cys Ser Arg
145                 150                 155                 160

Phe Tyr Leu Ser Lys Asn Gly Ser Arg Tyr Cys Ser Gly Tyr Phe Thr
                165                 170                 175

Asn Pro
```

```
<210> SEQ ID NO 14
<211> LENGTH: 1086
<212> TYPE: DNA
<213> ORGANISM: Lysobacter antibioticus

<400> SEQUENCE: 14

ggcggtcgtg atgcgaatgc agcagcaggt ctgagcggtc aggatctggt ttatagctac     60

gacgaaatgt ttgatttcga caccgcggcg tatctggcga aacatgcgcc gcacctggtt    120

cgtcatagcg aaagcattag ccactgggcg ggttacagca gcattagccc gaaagtgctg    180

atcgcgctga tggaacagca aagcggtgtt gtgagccgtc aacgtgcaag cgcagatgca    240

atgcgtcgtc cgtttggcaa actgagcgcg gcgaaagact tcaatagcca gacccgtgaa    300

gttgcgaccg cgctgcgtca ggcgctgtat gaacaagaag atgcgagcct ggcgccgcaa    360

ggtcgtgttc cgctggcacg tagcaacccg ctgcaggcgc tgtatctgca agcaggtgaa    420
```

-continued

```
agccaggcaa gcgcagcact gcgtggtgac ggcgaatttc agcaagtgta cggtcgtctg    480
ttcaatgaac cgcgtaaggc agcaccggca agcgcacgtt ttgcagatac cagcgatgtt    540
aatgcactgg caggtccggc gaatggcttt ctgcagttcc cgtatccgcg tggcgcgagc    600
tggcatgtgg gcggtgcgca caccaacacc ggtagcggca attacccgat gagcagcctg    660
gatatgagcc gtggcggtgg ctggggtagc aaccaaagcg gcaattgggt tagcgcgagc    720
gcgggtggca gctttaaacg tcatagcagc tgcttcgcgg aagttgtgca cagcggtggc    780
tggagcacca cctattacca tatgatgaac ctgcaatatg gtaccggtgc gagcgtggca    840
gcaaatagcc gtattggtaa tccggcaaat acccgtgcac aggcactgtg caatggtggc    900
gcgagcaccg gtccgcatga acactggagc ctgaaatata acggcagcca ttaccacctg    960
aatggtgttt atctgagcgg ctaccaaatc accgcgctgg gcagcagcta tgacaccaac   1020
tgcagccgtt tttacctgag caaaaatggt agccgttatt gcagcggcta cttcaccaat   1080
ccgtaa                                                              1086
```

<210> SEQ ID NO 15
<211> LENGTH: 1164
<212> TYPE: DNA
<213> ORGANISM: Lysobacter antibioticus

<400> SEQUENCE: 15

```
atgaaagcaa tctctaaagc aagattagga ttattagcat gctgcatcgc agcagcaatc     60
ggaggaacag caacagcagg cggtcgtgat gcgaatgcag cagcaggtct gagcggtcag    120
gatctggttt atagctacga cgaaatgttt gatttcgaca ccgcggcgta tctggcgaaa    180
catgcgccgc acctggttcg tcatagcgaa agcattagcc actgggcggg ttacagcagc    240
attagcccga aagtgctgat cgcgctgatg gaacagcaaa gcggtgttgt gagccgtcaa    300
cgtgcaagcg cagatgcaat gcgtcgtccg tttggcaaac tgagcgcggc gaaagacttc    360
aatagccaga cccgtgaagt tgcgaccgcg ctgcgtcagg cgctgtatga acaagaagat    420
gcgagcctgg cgccgcaagg tcgtgttccg ctggcacgta gcaacccgct gcaggcgctg    480
tatctgcaag caggtgaaag ccaggcaagc gcagcactgc gtggtgacgg cgaatttcag    540
caagtgtacg gtcgtctgtt caatgaaccg cgtaaggcag caccggcaag cgcacgtttt    600
gcagatacca gcgatgttaa tgcactggca ggtccggcga atggctttct gcagttcccg    660
tatccgcgtg gcgcgagctg gcatgtgggc ggtgcgcaca ccaacaccgg tagcggcaat    720
tacccgatga gcagcctgga tatgagccgt ggcggtggct ggggtagcaa ccaaagcggc    780
aattgggtta gcgcgagcgc gggtggcagc tttaaacgtc atagcagctg cttcgcggaa    840
gttgtgcaca gcggtggctg gagcaccacc tattaccata tgatgaacct gcaatatggt    900
accggtgcga gcgtggcagc aaatagccgt attggtaatc cggcaaatac ccgtgcacag    960
gcactgtgca atggtggcgc gagcaccggt ccgcatgaac actggagcct gaaatataac   1020
ggcagccatt accacctgaa tggtgtttat ctgagcggct accaaatcac cgcgctgggc   1080
agcagctatg acaccaactg cagccgtttt tacctgagca aaaatggtag ccgttattgc   1140
agcggctact tcaccaatcc gtaa                                          1164
```

<210> SEQ ID NO 16
<211> LENGTH: 575
<212> TYPE: DNA
<213> ORGANISM: Bacillus sp. KSM-S237
<220> FEATURE:
<223> OTHER INFORMATION: KSM-S237 promoter -continued

<400> SEQUENCE: 16

```
gatttgccga tgcaacaggc ttatatttag aggaaatttc tttttaaatt gaatacggaa     60

taaaatcagg taaacaggtc ctgattttat ttttttgagt tttttagaga actgaagatt    120

gaaataaaag tagaagacaa aggacataag aaaattgcat tagttttaat tatagaaaac    180

gcctttttat aattatttat acctagaacg aaaatactgt ttcgaaagcg gtttactata    240

aaaccttata ttccggctct tttttaaaac agggggtaaa aattcactct agtattctaa    300

tttcaacatg ctataataaa tttgtaagac gcaatatgca tctctttttt tacgatatat    360

gtaagcggtt aaccttgtgc tatatgccga tttaggaagg ggggtagatt gagtcaagta    420

gtaataatat agataactta taagttgttg agaagcagga gagcatctgg gttactcaca    480

agttttttta aaactttaac gaaagcactt tcggtaatgc ttatgaattt agctatttga    540

ttcaattact ttaaaaatat ttaggaggta atatg                               575
```

<210> SEQ ID NO 17
<211> LENGTH: 617
<212> TYPE: DNA
<213> ORGANISM: Bacillus sp. KSM-64
<220> FEATURE:
<223> OTHER INFORMATION: KSM-64 promoter

<400> SEQUENCE: 17

```
gaacaagtac ttaccatttt agagtcaaaa gatagaagcc aagcaggatt tgccgatgca     60

accggcttat atttagaggg aatttctttt taaattgaat acggaataaa atcaggtaaa    120

caggtcctga ttttattttt ttgaattttt ttgagaacta aagattgaaa tagaagtaga    180

agacaacgga cataagaaaa ttgtattagt tttaattata gaaaacgctt ttctataatt    240

atttatacct agaacgaaaa tactgtttcg aaagcggttt actataaaac cttatattcc    300

ggctcttttt ttaaacaggg ggtgaaaatt cactctagta ttctaatttc aacatgctat    360

aataaatttg taagacgcaa tatacatctt ttttttatga tatttgtaag cggttaacct    420

tgtgctatat gccgatttag gaagggggta gattgagtca agtagtcata atttagataa    480

cttataagtt gttgagaagc aggagagaat ctgggttact cacaagtttt ttaaaacatt    540

atcgaaagca ctttcggtta tgcttatgaa tttagctatt tgattcaatt actttaataa    600

ttttaggagg taatatg                                                   617
```

<210> SEQ ID NO 18
<211> LENGTH: 87
<212> TYPE: DNA
<213> ORGANISM: Bacillus sp. KSM-S237
<220> FEATURE:
<223> OTHER INFORMATION: KSM-S237 signal

<400> SEQUENCE: 18

```
atgttaagaa agaaaacaaa gcagttgatt tcttccattc ttattttagt tttacttcta     60

tctttatttc cggcagctct tgcagca                                         87
```

<210> SEQ ID NO 19
<211> LENGTH: 87
<212> TYPE: DNA
<213> ORGANISM: Bacillus sp. KSM-64
<220> FEATURE:
<223> OTHER INFORMATION: KSM-64 signal

<400> SEQUENCE: 19

-continued atgttaagaa agaaaacaaa gcagttgatt tcttccattc ttattttagt tttacttcta 60
tctttatttc cgacagctct tgcagca 87

<210> SEQ ID NO 20
<211> LENGTH: 74
<212> TYPE: DNA
<213> ORGANISM: Bacillus subtilis
<220> FEATURE:
<223> OTHER INFORMATION: amyE signal

<400> SEQUENCE: 20
atgtttgcaa aacgattcaa aacctcttta ctgccgttat tcgctggatt tttattgctg 60
tttcatttgg ttct 74

<210> SEQ ID NO 21
<211> LENGTH: 35
<212> TYPE: DNA
<213> ORGANISM: Artificial Sequence
<220> FEATURE:
<223> OTHER INFORMATION: BLP_S237signal_F

<400> SEQUENCE: 21
gaaggaaaca ctcgtatgaa aaaaatctca aaagc 35

<210> SEQ ID NO 22
<211> LENGTH: 36
<212> TYPE: DNA
<213> ORGANISM: Artificial Sequence
<220> FEATURE:
<223> OTHER INFORMATION: BLP_S237signal_R

<400> SEQUENCE: 22
aactagttta atagattagt tcggtccagg attcac 36

<210> SEQ ID NO 23
<211> LENGTH: 32
<212> TYPE: DNA
<213> ORGANISM: Artificial Sequence
<220> FEATURE:
<223> OTHER INFORMATION: vector-F

<400> SEQUENCE: 23
tctattaaac tagttatagg gttatctaaa gg 32

<210> SEQ ID NO 24
<211> LENGTH: 21
<212> TYPE: DNA
<213> ORGANISM: Artificial Sequence
<220> FEATURE:
<223> OTHER INFORMATION: vector-sig-R

<400> SEQUENCE: 24
acgagtgttt ccttctgctg c 21

<210> SEQ ID NO 25
<211> LENGTH: 29
<212> TYPE: DNA
<213> ORGANISM: Artificial Sequence
<220> FEATURE:
<223> OTHER INFORMATION: delta-BLPsig_F

<400> SEQUENCE: 25
tgcagcatct gctcagggac atggattaa 29

<210> SEQ ID NO 26
<211> LENGTH: 28
<212> TYPE: DNA
<213> ORGANISM: Artificial Sequence
<220> FEATURE:
<223> OTHER INFORMATION: delta-BLPsig_R

<400> SEQUENCE: 26
tgagcagatg ctgcaagagc tgccggaa 28

<210> SEQ ID NO 27
<211> LENGTH: 43
<212> TYPE: DNA
<213> ORGANISM: Artificial Sequence
<220> FEATURE:
<223> OTHER INFORMATION: BLPsig_F

<400> SEQUENCE: 27
ttaggaggta atatgatgaa aaaaatctca aaagctggtc tgg 43

<210> SEQ ID NO 28
<211> LENGTH: 37
<212> TYPE: DNA
<213> ORGANISM: Artificial Sequence
<220> FEATURE:
<223> OTHER INFORMATION: BLPsig_R

<400> SEQUENCE: 28
catattacct cctaaatatt tttaaagtaa ttgaatc 37

<210> SEQ ID NO 29
<211> LENGTH: 28
<212> TYPE: DNA
<213> ORGANISM: Artificial Sequence
<220> FEATURE:
<223> OTHER INFORMATION: delta-pro_F

<400> SEQUENCE: 29
ttgcagcatc tccgaatgga ctgcttca 28

<210> SEQ ID NO 30
<211> LENGTH: 27
<212> TYPE: DNA
<213> ORGANISM: Artificial Sequence
<220> FEATURE:
<223> OTHER INFORMATION: delta-pro_R

<400> SEQUENCE: 30
tcggagatgc tgcaagagct gccggaa 27

<210> SEQ ID NO 31
<211> LENGTH: 23
<212> TYPE: DNA
<213> ORGANISM: Artificial Sequence
<220> FEATURE:
<223> OTHER INFORMATION: delta-BLPsig2_F

<400> SEQUENCE: 31
tctgctcagg gacatggatt aag 23

<210> SEQ ID NO 32
<211> LENGTH: 48
<212> TYPE: DNA
<213> ORGANISM: Artificial Sequence
<220> FEATURE:
<223> OTHER INFORMATION: amyEsig(BLP)_F

<400> SEQUENCE: 32
ttaggaggta atatgatgtt tgcaaaacga ttcaaaacct ctttactg 48

<210> SEQ ID NO 33
<211> LENGTH: 34
<212> TYPE: DNA
<213> ORGANISM: Artificial Sequence
<220> FEATURE:
<223> OTHER INFORMATION: amyEsig(BLP)_R

<400> SEQUENCE: 33
atgtccctga gcagaagcac tcgcagccgc cggt 34

<210> SEQ ID NO 34
<211> LENGTH: 55
<212> TYPE: DNA
<213> ORGANISM: Artificial Sequence
<220> FEATURE:
<223> OTHER INFORMATION: BLP_FLAG_F

<400> SEQUENCE: 34
acaaagatga tgatgataaa taatctatta aactagttat agggttatct aaagg 55

<210> SEQ ID NO 35
<211> LENGTH: 37
<212> TYPE: DNA
<213> ORGANISM: Artificial Sequence
<220> FEATURE:
<223> OTHER INFORMATION: BLP_FLAG_R

<400> SEQUENCE: 35
catcatcatc tttgtaatcg ttcggtccag gattcac 37

<210> SEQ ID NO 36
<211> LENGTH: 30
<212> TYPE: DNA
<213> ORGANISM: Artificial Sequence
<220> FEATURE:
<223> OTHER INFORMATION: LasA_F

<400> SEQUENCE: 36
gcagctcttg cagcacatga tgatggcctg 30

<210> SEQ ID NO 37
<211> LENGTH: 45
<212> TYPE: DNA
<213> ORGANISM: Artificial Sequence
<220> FEATURE:
<223> OTHER INFORMATION: LasA_CR

<400> SEQUENCE: 37
tagtttaata gattagtggt ggtggtggtg cagagccagt cccgg 45

<210> SEQ ID NO 38
<211> LENGTH: 35
<212> TYPE: DNA
<213> ORGANISM: Artificial Sequence
<220> FEATURE:
<223> OTHER INFORMATION: pHY_just_F

<400> SEQUENCE: 38
taatctatta aactagttat agggttatct aaagg 35

<210> SEQ ID NO 39
<211> LENGTH: 21

<212> TYPE: DNA
<213> ORGANISM: Artificial Sequence
<220> FEATURE:
<223> OTHER INFORMATION: pHY_just_R_NEW

<400> SEQUENCE: 39
tgctgcaaga gctgccggaa a 21

<210> SEQ ID NO 40
<211> LENGTH: 22
<212> TYPE: DNA
<213> ORGANISM: Artificial Sequence
<220> FEATURE:
<223> OTHER INFORMATION: LasA_Chis_n_R

<400> SEQUENCE: 40
cagagccagt cccggattat ac 22

<210> SEQ ID NO 41
<211> LENGTH: 31
<212> TYPE: DNA
<213> ORGANISM: Artificial Sequence
<220> FEATURE:
<223> OTHER INFORMATION: AhP_F

<400> SEQUENCE: 41
ttaggaggta atatgatgtc tcgtccgatc c 31

<210> SEQ ID NO 42
<211> LENGTH: 30
<212> TYPE: DNA
<213> ORGANISM: Artificial Sequence
<220> FEATURE:
<223> OTHER INFORMATION: AhP_R

<400> SEQUENCE: 42
aactagttta atagattagt cgattccgtt 30

<210> SEQ ID NO 43
<211> LENGTH: 33
<212> TYPE: DNA
<213> ORGANISM: Artificial Sequence
<220> FEATURE:
<223> OTHER INFORMATION: vector-R

<400> SEQUENCE: 43
catattacct cctaaatatt tttaaagtaa ttg 33

<210> SEQ ID NO 44
<211> LENGTH: 33
<212> TYPE: DNA
<213> ORGANISM: Artificial Sequence
<220> FEATURE:
<223> OTHER INFORMATION: LgBLP_F

<400> SEQUENCE: 44
gcagctcttg cagcagcgga acgtggtctg agc 33

<210> SEQ ID NO 45
<211> LENGTH: 35
<212> TYPE: DNA
<213> ORGANISM: Artificial Sequence
<220> FEATURE:
<223> OTHER INFORMATION: LgBLP_R

<400> SEQUENCE: 45

-continued

```
tagtttaata gattagtgac ccggattggt gaacc                          35


<210> SEQ ID NO 46
<211> LENGTH: 34
<212> TYPE: DNA
<213> ORGANISM: Artificial Sequence
<220> FEATURE:
<223> OTHER INFORMATION: LaBLP_F

<400> SEQUENCE: 46

gcagctcttg cagcaggcgg tcgtgatgcg aatg                           34


<210> SEQ ID NO 47
<211> LENGTH: 34
<212> TYPE: DNA
<213> ORGANISM: Artificial Sequence
<220> FEATURE:
<223> OTHER INFORMATION: LaBLP_R

<400> SEQUENCE: 47

tagtttaata gattacggat tggtgaagta gccg                           34


<210> SEQ ID NO 48
<211> LENGTH: 35
<212> TYPE: DNA
<213> ORGANISM: Artificial Sequence
<220> FEATURE:
<223> OTHER INFORMATION: delta-S237N_fw

<400> SEQUENCE: 48

tgcagcaatg aaaaaaatct caaaagctgg tctgg                          35


<210> SEQ ID NO 49
<211> LENGTH: 28
<212> TYPE: DNA
<213> ORGANISM: Artificial Sequence
<220> FEATURE:
<223> OTHER INFORMATION: delta-S237N_rv

<400> SEQUENCE: 49

tttttcattg ctgcaagagc tgccggaa                                  28


<210> SEQ ID NO 50
<211> LENGTH: 45
<212> TYPE: DNA
<213> ORGANISM: Artificial Sequence
<220> FEATURE:
<223> OTHER INFORMATION: 2R_bacillus-Chis

<400> SEQUENCE: 50

aactagttta atagattagt ggtggtggtg gtggtcgatt ccgtt               45
```